(12) United States Patent
Inoue et al.

(10) Patent No.: US 7,915,030 B2
(45) Date of Patent: Mar. 29, 2011

(54) METHOD AND MOLECULAR DIAGNOSTIC DEVICE FOR DETECTION, ANALYSIS AND IDENTIFICATION OF GENOMIC DNA

(75) Inventors: Hiroshi Inoue, Bethesda, MD (US); Ivor T. Knight, Arlington, VA (US); Gregory A. Dale, Gaithersburg, MD (US); Rita R. Colwell, Bethesda, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 1244 days.

(21) Appl. No.: 11/514,156

(22) Filed: Sep. 1, 2006

(65) Prior Publication Data

US 2007/0111303 A1    May 17, 2007

Related U.S. Application Data

(60) Provisional application No. 60/712,813, filed on Sep. 1, 2005.

(51) Int. Cl.
*C12M 1/34* (2006.01)
*C12M 3/00* (2006.01)

(52) U.S. Cl. .................................. 435/287.2

(58) Field of Classification Search ........... 435/6, 287.1–287.2, 288.5, 288.7
See application file for complete search history.

(56) References Cited

U.S. PATENT DOCUMENTS

| | | | |
|---|---|---|---|
| 4,313,124 A | 1/1982 | Hara | |
| 4,345,262 A | 8/1982 | Shirato et al. | |
| 4,459,600 A | 7/1984 | Sato et al. | |
| 4,463,359 A | 7/1984 | Ayata et al. | |
| 4,558,333 A | 12/1985 | Sugitani et al. | |
| 4,723,129 A | 2/1988 | Endo et al. | |
| 4,740,796 A | 4/1988 | Endo et al. | |
| 5,714,380 A * | 2/1998 | Neri et al. | 435/287.2 |
| 5,965,410 A | 10/1999 | Chow et al. | |
| 6,033,546 A | 3/2000 | Ramsey | |
| 6,238,538 B1 | 5/2001 | Parce et al. | |
| 6,267,858 B1 | 7/2001 | Parce et al. | |
| 6,500,323 B1 | 12/2002 | Chow et al. | |
| 6,534,262 B1 * | 3/2003 | McKernan et al. | 435/6 |
| 6,582,576 B1 | 6/2003 | Chow et al. | |
| 6,670,153 B2 | 12/2003 | Stern | |
| 6,681,788 B2 | 1/2004 | Parce et al. | |
| 6,779,559 B2 | 8/2004 | Parce et al. | |
| 6,787,088 B2 | 9/2004 | Parce et al. | |
| 2001/0052460 A1 | 12/2001 | Chien et al. | |
| 2002/0150907 A1 * | 10/2002 | Fomovskaia et al. | 435/6 |
| 2003/0054395 A1 | 3/2003 | Baker | |
| 2003/0130499 A1 | 7/2003 | Baker | |
| 2004/0152076 A1 * | 8/2004 | Willson et al. | 435/6 |

FOREIGN PATENT DOCUMENTS

WO    WO97/41219    * 4/1997

* cited by examiner

*Primary Examiner* — Walter D Griffin
*Assistant Examiner* — Shanta G Doe
(74) *Attorney, Agent, or Firm* — Rothwell, Figg, Ernst & Manbeck, pc

(57) ABSTRACT

At least one exemplary embodiment of the invention is directed to a molecular diagnostic device that comprises a cartridge configured to eject samples comprising genomic material into a microfluidic chip that comprises an amplification area, a detection area, and a matrix analysis area.

33 Claims, 13 Drawing Sheets

METHOD AND MOLECULAR DIAGNOSTIC DEVICE FOR DETECTION, ANALYSIS AND IDENTIFICATION OF GENOMIC DNA

RELATED APPLICATIONS

This application claims the benefit of priority from U.S. Provisional Patent Application No. 60/712,813, filed Sep. 1, 2005, the content of which is hereby incorporated by reference herein in its entirety.

BACKGROUND OF THE INVENTION

1. Field of the Invention

The invention is directed toward a molecular diagnostic device that can be used to characterize genomic material that may be present in a sample.

2. Related Background Art

In the biotechnological field, there is a need for rapid identification of organisms, such as bacteria and viruses, in a variety of samples (e.g., environmental and medical). For example, rapid characterization of genomic material isolated from a bacterium (i.e., identification of the species and/or strain of the bacterium) may be necessary to provide quality assurance for, e.g., a local water supply, a hospital (including hospitalized patients therein), or a food processing plant; i.e., it may be necessary to monitor various samples, including but not limited to samples of air, dust, water, blood, tissues, plants, foodstuffs, etc., for the presence of contaminating organisms, and to identify the contaminating organisms prior to consumption, exposure, and/or use by the public, or during use by the public, or in tissue or blood samples obtained from a patient or another member of the public.

Standard microbiological methods for identifying an organism, e.g., culturing and Gram-staining or testing of other biochemical properties, are imprecise and often cannot differentiate among different organisms, let alone different strains of an organism. More precise methods for identifying an organism are based on the genomic DNA of the organism. Two such methods of identification are the polymerase chain reaction (PCR), for which technological developments (e.g., automated inline PCR platforms) have increased its level of throughput and automation, and the newer method of waveform profiling.

Because PCR exponentially amplifies DNA, it can be used to detect small amounts of genomic material. However, because PCR requires primers that are specifically complimentary to sequences of the genomic material that are known and bracket a DNA locus of interest, PCR is limited in that it can only be used for the characterization of known organisms. In other words, the investigator is required to know or guess the identity of the organism (i.e., the appropriate pair of primers to use) prior to any attempts at detecting the organism. Another limitation of PCR is the inability of the investigator, without further study, to map and/or obtain sequence information about the amplified DNA (and consequently the isolated genomic material) other than information about the sequences complimentary to the two primers used in the analysis. Additionally, an automated inline PCR platform generally does not provide a means to further analyze (e.g., map) genomic material after it has been subjected to PCR. Further analysis (e.g., providing more certain identification of a species and/or strain) of the genomic material may be important and useful in, e.g., distinguishing a pathogenic strain from a nonpathogenic strain, detecting and providing the sequence of a new strain, choosing an appropriate antibiotic regimen, etc.

To overcome some of the limitations of PCR, methods of waveform profiling were developed (see, e.g., U.S. patent application Ser. Nos. 11/190,942 and 11/356,807, and Japanese Patent Application Publication Nos. 2003-334082 and 2003-180351). Waveform profiling methods provide ways to analyze and profile genomic material, e.g., DNA isolated from organisms, such as bacteria, without requiring the investigator to know the identity of the organism prior to detection.

Waveform profiling generally utilizes melting temperature analysis accomplished with the use of detectable (e.g., radioactive, fluorescent, chemiluminescent, etc.) agents (e.g., nucleotides, intercalators, etc.) that are incorporated into higher-order DNA structures generated by waveform profiling. As the temperature of the sample is increased, the higher-order structures dissociate and, e.g., lose fluorescence intensity (e.g., intercalated fluorescent agents dissociate). Plotting the rate of change of fluorescence intensity obtained by the dissociation of these higher-order structures as a function of increasing temperature produces a waveform unique to the genomic DNA of the organism and the utilized waveform primer, i.e., the dissociation of higher-order DNA structures at different melting temperatures (Tm) is observed and recorded to produce a characteristic "waveform profile" for each species (or strain) of organism, e.g., bacteria. Accordingly, waveform profiling can be used to distinguish between genomic DNA isolated from a first organism and genomic DNA isolated from a second organism using melting temperature analysis. However, waveform profiling does not provide, without further investigation, the map or sequence of the analyzed genomic material.

Since waveform profiling is a relatively new method, advances described herein can be used to increase its throughput and/or automation.

As discussed above, new technologies that increase the level of PCR throughput and automation have been developed. An example of one such technology is the use of microfluidic systems, including controller/detector interfaces for such microfluidic systems, as described in, e.g., U.S. Pat. Nos. 6,033,546; 6,238,538; 6,267,858; 6,500,323; and 6,670,153. These microfluidic systems, collectively referred to herein as automated inline PCR platforms, are well known in the art and are generally described herein.

Most automated inline PCR platforms utilize a disposable microfluidic chip that works with controller/detector interfaces for automated sample accession, microfluidic PCR reagent assembly, PCR thermal cycling, and optical detection spectroscopy. A microfluidic chip generally comprises a first plate with at least one micro-etched fluidic (microfluidic) inline reaction channel that can be bonded to a second plate, within which can be metal traces and a fluid reservoir. When the two plates are bonded together, each microfluidic reaction channel of the first plate can connect with a fluid reservoir of the second plate so that locus-specific reagents can be delivered through the fluid reservoirs to the microfluidic inline reaction channels.

Inline PCR begins when a capillary, or "sipper," aspirates a sample droplet (which may or may not be a DNA sample droplet, i.e., a sample droplet comprising genomic material isolated from an organism) from, e.g., a microtiter plate, into at least one microfluidic inline reaction channel. After aspirating a sample droplet into a microfluidic inline reaction channel, the sipper can be moved to a buffer trough so that buffer is drawn into the microfluidic chip. Consequently, cross-contamination among sample droplets is minimized or eliminated since each sample droplet is separated from adjacent sample droplets by buffer spacers. Each sample droplet then moves along a microfluidic inline reaction channel and into a PCR assembly area of the chip, wherein the sample droplet becomes a sample plug by being mixed with PCR-required reagents, e.g., a primer pair, DNA polymerase, and dNTPs, and detectable agents, e.g., intercalators, etc. Optionally, buffer spacers can also be mixed with PCR-required reagents to serve as negative controls. After being mixed with PCR-required and detectable agents, a sample plug (which may or may not be a DNA sample plug, i.e., a sample plug comprising genomic material) moves along the length of the microfluidic inline reaction channel into different areas of the chip, e.g., an amplification area wherein PCR can be effected on the sample plugs.

Generally, as each sample plug (e.g., a DNA sample plug) flows through a microfluidic inline reaction channel, it enters a temperature-controlled amplification area wherein each microfluidic inline reaction channel is repeatedly and rapidly heated and cooled in a localized manner such that the denaturing, annealing and elongation steps of PCR are effected on the sample plugs as they move through the channel(s); sample plugs that do not comprise genomic material are exposed to the same heating and cooling processes, etc. Amplification of DNA will occur only in DNA sample plugs, i.e., sample plugs comprising genomic material. A method of controlling the temperature in the amplification area is Joule heating (see, e.g., U.S. Pat. Nos. 5,965,410 and 6,670,153). Generally, voltage can be applied to the metal traces in or near the microfluidic inline reaction channel in a controlled and localized manner to effectuate the different temperatures required for each PCR cycle. Cooling of the reaction can be achieved through the use of, e.g., cooling fluid that travels through a coil to carry away thermal energy from the microfluidic inline reaction channel, rapid heat dissipation, e.g., by application of cold water to the bottom surface of the microfluidic chip, or simple radiant convection into the atmosphere or suitable heat transfer using a heat sink. Since the volume of fluid in the microfluidic channels is small and the metal traces are located very close to the microfluidic inline reaction channels, heating and cooling of the fluid in the channels (and hence, sample plugs) is accomplished very rapidly. Consequently, DNA sample plugs undergo PCR, and PCR cycles run such that, e.g., 30 cycles can typically be performed in, e.g., less than nine minutes. The number of PCR cycles each DNA sample plug sees as it travels through a microfluidic channel in the temperature-controlled area of the chip can be varied by changing, e.g., either or both 1) the timing of the voltage applied to the metal traces, and 2) the flow rate of the DNA sample plugs through the microfluidic channels.

A microfluidic chip can simultaneously perform as many polymerase chain reactions as it has microfluidic inline reaction channels. For example, a sample comprising genomic material can be aspirated into multiple different microfluidic inline reaction channels, to each of which is added a different locus-specific reagent (e.g., a different primer pair that brackets a different locus on the genomic material, e.g., DNA). This permits simultaneously detecting several different loci of genomic material isolated from the same organism. Alternatively, reagents comprising one specific primer pair can be aspirated into multiple different microfluidic inline reaction channels. This permits simultaneously detecting the same locus on genomic material isolated from different samples and/or different organisms. Additionally, multiple sample droplets can be aspirated into the same microfluidic reaction channel.

A detection area is usually downstream of the temperature-controlled amplification area, and is generally a transparent region that facilitates observation and detection of the amplified DNA products, e.g., PCR products. In the detection area, each microfluidic inline reaction channel is usually brought in close proximity and passed under a detector. A light source spreads light across the microfluidic inline reaction channels so that detectable agents or energy, e.g., fluorescence emitted from each channel, e.g., from each DNA sample plug, passing through the optical detection area can be measured simultaneously. After detection, each microfluidic inline reaction channel usually directs each sample plug to a waste well.

Three different methods are usually used to generate fluid motion within microfluidic inline reaction channels; the methods involve electrokinetics, pressure, or a hybrid of the two (see, e.g., U.S. Pat. Nos. 6,238,538; 6,670,153; 6,787,088; and U.S. Published patent application No. 2001/0052460) and nonmechanical valves (see, e.g., U.S. Pat. Nos. 6,681,788 and 6,779,559). In a pressure-based flow system, an internal or external source can be used to drive the flow of fluid in the inline reaction channels. For example, a vacuum can be applied to waste wells at the ends of each microfluidic inline reaction channel and can be used to activate the sipper and move the fluid along the microfluidic inline reaction channels toward the waste wells. Alternatively, since genomic material is charged, electrokinetics, i.e., the generation of a voltage gradient (e.g., by the application of voltage to the metal traces) can be used to drive charged fluid along the microfluidic inline reaction channels. A third method of driving the fluid along the inline reaction channels uses both electrokinetics and pressure. The result is a continuous flow of fluid within the microfluidic inline reaction channels, wherein sample plugs (e.g., DNA sample plugs) are continuously being mixed or moved to different areas (e.g., a PCR assembly area, a temperature-controlled area, a detection area, etc.) of the chip.

Electrokinetic and/or pressure-driven fluid movement, heating and cooling cycles, detection, and the data acquisition related to a microfluidic chip can be controlled by an instrument that interfaces with the chip (generally described in, e.g., U.S. Pat. Nos. 6,033,546 and 6,582,576). The interface of the instrument usually contains o-ring seals that seal the reagent wells on the chip, pogo pins that can interface with the metal traces on the chip and supply the voltage for temperature cycling, o-ring seals for the waste wells where a vacuum can be applied to move the fluid through the chip, a large o-ring that can be used to seal the bottom of the chip against circulating cool water and to speed the cooling during the temperature cycling, and a detection zone for, e.g., fluorescence detection. The risk of contamination with this system is minimal because a microfluidic chip is usually a closed system with physical barriers (e.g., buffer spacers) separating DNA sample plugs. Moreover, continuous flow prevents sample plugs from moving backwards.

The automated inline PCR platforms described above are limited in that the microfluidic chips should be disposed of after use and are not suitable for automated inline waveform profiling; also, analyzing samples using such a platform requires outsourcing. Additionally, the use of a sipper to aspirate sample droplets is an inefficient and wasteful method to obtain the small volume required to effect PCR cycles rapidly. The present invention resolves these limitations by providing a molecular diagnostic device that can be used to characterize genomic material isolated from an organism (e.g., bacteria, viruses) in a sample by automated methods of preparing the genomic material, and then either or both 1) amplifying the genomic material and detecting any amplified products and 2) mapping the genomic material. A molecular diagnostic device of at least one exemplary embodiment of the invention has the advantage that multiple samples, e.g., patient samples, can be processed through the same microfluidic chip without cross-contamination. Also, because in some exemplary embodiments the device is a portable system, a device of at least one exemplary embodiment of the invention can be utilized at different patient care centers throughout the Unites States or elsewhere in the world, and can also be used in a near-patient setting or a contaminated site away from a hospital or other patient care center. The molecular diagnostic device disclosed herein also has the advantage of facilitating the screening of samples within a short time after collection.

SUMMARY OF THE INVENTION

At least one exemplary embodiment is directed to a cartridge configured for isolating genomic material, wherein the cartridge comprises at least one channel and a solid substrate capable of binding and releasing genomic material. In at least one further exemplary embodiment, the cartridge further comprises a waste well. In another exemplary embodiment, the solid substrate capable of binding and releasing genomic material (i.e., binding and release substrate) comprises charge switch material.

At least one exemplary embodiment of the invention is directed to a cartridge configured to isolate genomic material comprising: a reaction chamber, and at least one binding and release substrate, wherein the at least one binding and release substrate lies within the reaction chamber and is configured to bind and release at least a portion of a sample comprising genomic material. In at least one other exemplary embodiment, the substrate comprises charge switch material. In at least one further exemplary embodiment, the binding and releasing of at least a portion of the sample is in response to an electric voltage. In at least one other further exemplary embodiment, the binding and releasing of at least a portion of the sample is in response to a difference in ionic composition of a fluid in contact with the substrate, and the sample is contained within the fluid. In at least one other further exemplary embodiment, the binding and releasing of at least a portion of the sample is in response to a difference in pH of a fluid in contact with the substrate, and the sample is contained within the fluid. In at least one other exemplary embodiment, the substrate is a particle or bead. In at least one other further exemplary embodiment, the substrate is magnetic or paramagnetic. In at least one other further exemplary embodiment, the substrate is bound to the inner surface of the reaction chamber. In at least one other exemplary embodiment, the volume of at least a portion of the sample released from the substrate is reduced from the volume of the sample.

At least one exemplary embodiment of the invention is directed to a cartridge, configured to deliver a sample comprising genomic material, comprising a genomic separation and direction system, and an ejector head, wherein a chamber in the ejector head is configured to receive at least a portion of a sample comprising genomic material from the genomic separation and direction system, and wherein the ejector head expels at least a portion of the received sample out of the cartridge as ejected sample droplets. In at least one other exemplary embodiment, the ejector head uses thermal energy provided by a thermal energy generator. In at least one further exemplary embodiment, the ejector head is a piezo jet system.

At least one exemplary embodiment of the invention is directed to a cartridge configured to isolate genomic material comprising a reaction chamber, at least one binding and release substrate, wherein the at least one binding and release substrate lies within the reaction chamber and is configured to bind and release at least a portion of a sample comprising genomic material in response to an electric voltage, a genomic separation and direction system, and an ejector head, wherein a chamber in the ejector head is configured to receive at least a portion of the sample from the genomic separation and direction system, and wherein the ejector head expels at least a portion of the received sample out of the cartridge as ejected sample droplets. In at least one other exemplary embodiment, the substrate comprises charge switch material. In at least one further exemplary embodiment, the substrate is a particle or bead. In at least one other further exemplary embodiment, the substrate is magnetic or paramagnetic. In at least one other exemplary embodiment, the substrate is bound to the inner surface of the reaction chamber. In at least one other exemplary embodiment, the ejector head uses thermal energy provided by a thermal energy generator. In at least one further exemplary embodiment, the ejector head is a piezo jet system.

At least one exemplary embodiment of the invention is directed to a molecular diagnostic device comprising at least one cartridge and at least one microfluidic chip, wherein the chip is configured to receive at least a portion of the sample droplets ejected from the cartridge, and wherein the chip comprises at least one microfluidic inline reaction channel for receiving the sample droplets ejected from the cartridge. In at least one other exemplary embodiment, the ejector head of the cartridge can be repetitively pulsed to form multiple droplets in sequence at a repetitive pulse rate to achieve a controlled total droplet volume in the microfluidic inline reaction channel of the microfluidic chip. In at least one further exemplary embodiment, the repetitive pulse rate is in the range of about 1 kHz to about 100 kHz. In at least one other further exemplary embodiment, the repetitive pulse rate is about 50 kHz. In at least one other exemplary embodiment, an ejected sample droplet has a volume in the range of about 1 picoliter to about 25 picoliters. In at least one other further exemplary embodiment, the ejected sample droplet has a volume of about 3 picoliters. In at least one other exemplary embodiment, the total droplet volume is in the range about 3 picoliters to about 100 nanoliters. In at least one further exemplary embodiment, the microfluidic chip further comprises an amplification area within a first temperature-controlled area for the amplification of DNA products, and a detection area within a second temperature-controlled area, and detection of amplified DNA products can occur at more than one temperature. In at least one other exemplary embodiment, the device further comprises a matrix analysis area.

At least one exemplary embodiment of the invention is directed to a microfluidic chip comprising a sample droplet receiving system configured to receive at least a portion of sample droplets comprising genomic material ejected by a cartridge, and a matrix analysis area, wherein the matrix analysis area comprises an emitter layer, a filter layer, and a detector layer, wherein the emitter layer emits an emitter wavelength. In at least one other exemplary embodiment, the filter layer comprises an optical filter doped glass that passes a fluorescent wavelength and blocks the emitter wavelength. In at least one other exemplary embodiment, the microfluidic chip further comprises at least two channels, wherein the two channels are configured to flow samples comprising genomic material through an amplification area within a first temperature-controlled area for the amplification of DNA products, and a detection area within a second temperature-controlled area for the initiation of fluorescence of DNA products, and wherein detection of amplified DNA products can occur at more than one temperature.

At least one exemplary embodiment of the invention is directed to a molecular diagnostic device comprising at least one cartridge and a microfluidic chip, wherein the cartridge ejects sample droplets comprising genomic material into the sample droplet receiving system of the microfluidic chip. In at least one other exemplary embodiment, the matrix analysis area further comprises more than one unit, and each unit comprises at least one photon generator component, a DNA stretchchip, and at least one photon detector component. In at least one further exemplary embodiment, the at least one photon detector component comprises porphyrin gate material. In at least one other exemplary embodiment, the at least one photon detector component comprises three thin-film transistors. In at least one other further exemplary embodiment, the device is portable. In at least one further exemplary embodiment, the device is hand-held.

At least one exemplary embodiment of the invention is directed to a method of characterizing genomic material in a sample, comprising the steps of (a) isolating any genomic material in the sample with a cartridge; (b) ejecting at least one sample droplet from a liquid ejection mechanism in the cartridge into a sample droplet receiving system of a microfluidic chip; (c) detecting genomic material in the sample droplet; and (d) analyzing the sample droplet to characterize the genomic material present. In at least one other exemplary embodiment, analyzing the sample droplet comprises comparing a detected barcode from the genomic material in the sample with a database of known barcodes.

At least one exemplary embodiment of the invention is directed to a molecular diagnostic device comprising at least one cartridge for isolating genomic material; at least one sample droplet ejection head for ejecting the genomic material from the cartridge after it is isolated, wherein the at least one cartridge can be attached to at least one sample droplet ejection head; and at least one microfluidic chip for analyzing the genomic material, wherein the microfluidic chip comprises at least one microfluidic inline reaction channel for receiving the ejected genomic material from the sample droplet ejection head and at least one metal trace for heating of and/or fluid movement within the microfluidic inline reaction channel, and wherein the at least one microfluidic inline reaction channel runs through a reagent assembly area, an amplification area within a first temperature-controlled area for the amplification of DNA products, and a detection area. In at least one further exemplary embodiment, the detection area is within a second temperature-controlled area, and the detection of amplified DNA products can occur at more than one temperature. In another exemplary embodiment, the device further comprises a matrix analysis area. In a further exemplary embodiment, the matrix analysis area comprises more than one unit, and each unit comprises at least one photon generator component, a DNA stretchchip, and at least one photon detector component. In another exemplary embodiment of the invention, the molecular diagnostic device is portable. In another further exemplary embodiment, the matrix analysis area of the molecular diagnostic device comprises a matrix of 512×512 units.

BRIEF DESCRIPTION OF THE DRAWINGS

FIG. 6A depicts a representation of a 2×2 matrix, including representations of row wiring (RW) and column wiring (CW), as well as the timing chart (Timing Chart 2) for the clock pulses OUT1 and OUT2 from a binary shift register (BSR1). FIG. 6B depicts Timing Charts 1 and 4, and FIG. 6C depicts Timing Chart 3 (which follows the status of pulses IN1 and IN2 from BSR2 (as shown in FIG. 6A)).

DETAILED DESCRIPTION OF THE INVENTION

Figure 1A:
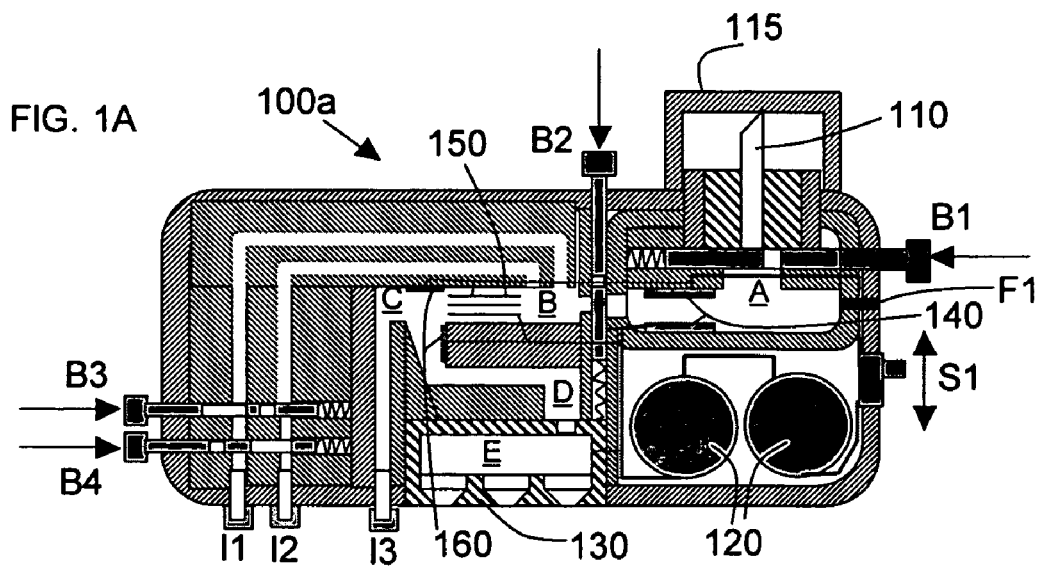
FIG. 1A illustrates a cartridge design in accordance with at least one exemplary embodiment of the invention.

The following description of at least one exemplary embodiment is merely illustrative in nature and is in no way intended to limit the invention, its application, or uses.

Processes, techniques, apparatus, and materials as known by one of ordinary skill in the relevant art may not be discussed in detail but are intended to be part of the enabling description where appropriate, for example, the fabrication of microfluidic channels, subchannels, and microchannels and their related materials.

In all of the examples illustrated and discussed herein, any specific values, for example, the amount of fluid (e.g., picoliters), should be interpreted to be illustrative only and nonlimiting. Thus, other examples of the exemplary embodiments could have different values.

Note that similar reference numbers and letters refer to similar items in the figures disclosed and discussed herein, and thus once an item is defined in one figure, it may not be discussed for following figures.

At least one exemplary embodiment of the present invention is directed to a molecular diagnostic device and methods of using the molecular diagnostic device for automated methods of characterizing genomic material in a sample. In a broad exemplary embodiment, the method entails preparing sample genomic material (i.e., isolating any material, and portioning the sample(s)) and identifying the genomic material by (either or both) 1) amplification and detection of amplified products and 2) mapping. The molecular diagnostic device of at least one exemplary embodiment of the invention comprises at least one cartridge and at least one liquid ejection mechanism for the preparation (isolation and partitioning of genomic material of a sample to be analyzed); and at least one microfluidic chip for amplification of genomic material isolated from the sample and detection of products amplified from the genomic material. In at least one exemplary embodiment of the invention, the liquid ejection mechanism transfers a prepared sample from the cartridge to the microfluidic chip. In another exemplary embodiment of the invention, a molecular diagnostic device of the invention further comprises a matrix analysis area for mapping of the genomic material. Thus, a molecular diagnostic device of at least one exemplary embodiment of the invention can be used for an automated method of characterizing genomic material, the method comprising the steps of preparing the genomic material and either or both 1) amplifying the genomic material and detecting the amplified products and 2) mapping the genomic material.

It will be easily recognized that for purposes herein, the step of preparing a sample comprises isolating genomic material, if present, from the sample, and partitioning the sample (including any isolated genomic material) for analysis. Also the step of amplifying the genomic material comprises mixing any isolated genomic material with appropriate amplification reagents (e.g., primers, dNTPs, salts, buffers, etc.) and optionally detection reagents (e.g., intercalators) and effecting an amplification reaction on the isolated genomic material. Nonlimiting examples of amplification reactions that can be performed with a molecular diagnostic device of at least one exemplary embodiment of the invention include PCR and various forms of waveform profiling (see, e.g., U.S. patent application Ser. Nos. 11/190,942 and 11/356,807, the contents of which are hereby incorporated by reference herein in their entireties). The step of detecting is dependent on the amplification method used, i.e., whether a PCR product or the dissociation of higher-order structures is detected depends on whether PCR or a waveform profiling method, respectively, is performed. After a sample is prepared, a molecular diagnostic device of at least one exemplary embodiment of the invention will permit any isolated genomic material to 1) be amplified and detected via its amplified products, 2) be amplified and detected via its amplified products, and mapped within the matrix analysis area, described herein, or 3) be mapped within the matrix analysis area, described herein.

Molecular Diagnostic Device

Over the last few years, automated inline PCR platforms have been developed for compatibility with a variety of existing and well-known fluorescent "mix-and-read" biochemistries, such as TaqMan, Molecular Beacons, Epoch Eclipse Probes, and Allele Specific Amplification. To date, no known automated inline platform has allowed efficient on-site (e.g., near-patient) genetic testing that would obviate the need to outsource samples, e.g., patient samples collected at a doctor's office or at another near-patient site. It is an object of the invention to provide a molecular diagnostic device that can be used, e.g., to analyze a patient sample for, e.g., the presence of bacterial or viral infection, at the same place and within a short time frame (e.g., approximately one hour) of the procurement of the sample to be analyzed. As described in further detail herein, a molecular diagnostic device of at least one exemplary embodiment of the invention comprises at least one cartridge configured for isolating any genomic material present in a sample; at least one liquid ejection mechanism comprising at least one ejection head for partitioning any isolated genomic material, wherein the at least one cartridge can be or is temporarily attached to the at least one ejection head; and at least one microfluidic chip for detecting any genomic material, wherein the microfluidic chip comprises at least one microfluidic inline reaction channel for receiving the ejected genomic material from the liquid ejection mechanism and at least one metal trace for heating of and/or fluid movement within the microfluidic inline reaction channel, and wherein the at least one microfluidic inline reaction channel runs through a reagent assembly area, an amplification area within a first temperature-controlled area for the amplification of DNA products, and a detection area of the microfluidic chip. In another exemplary embodiment of the invention, a molecular diagnostic device of the invention further comprises a matrix analysis area for genomic mapping.

1. Preparing Genomic Material

The molecular diagnostic device of at least one exemplary embodiment of the invention comprises a cartridge and a liquid ejection mechanism, both of which are involved particularly in the step of preparing any genomic material present in a sample. In other words, the genomic material can be isolated from a collected sample (e.g., a patient sample) via a cartridge and subsequently ejected via the liquid ejection mechanism prior to the later steps of amplifying and detecting (and/or mapping) via a microfluidic chip.

It is contemplated by the inventors that a molecular diagnostic device of at least one exemplary embodiment of the invention can be used for on-site (e.g., near-patient) testing of patient samples; in addition, many different types of samples can be tested using a molecular diagnostic device of the invention. Such samples include, but are not limited to, water, air, dust, food, and biological samples, including body fluids (e.g., saliva, whole blood, plasma, buffy coat, urine, etc.), cells (e.g., whole cells, cell fractions, and cell extracts), and tissues. Biological samples also include sections of tissue such as biopsies and frozen sections taken, e.g., for histological purposes. Exemplary biological samples include, but are not limited to, blood, plasma, lymph, tissue biopsies, urine, CSF (cerebrospinal fluid), synovial fluid, and BAL (bronchioalveolar lavage). In at least one exemplary embodiment of the invention, the biological sample is blood.

A. Cartridge

The sample can be collected utilizing any well-known method(s), e.g., a syringe for the collection of a patient blood sample, and then placed into a disposable cartridge of at least one exemplary embodiment of the invention for the isolation of genomic material from the sample; in at least one exemplary embodiment, the sample is collected directly into the disposable cartridge. A cartridge of at least one exemplary embodiment of the invention is configured to isolate any genomic material contained in a sample and comprises at least one channel (and/or chamber) within the cartridge; genomic material is isolated from a sample in the at least one channel within the cartridge.

Figure 1B:
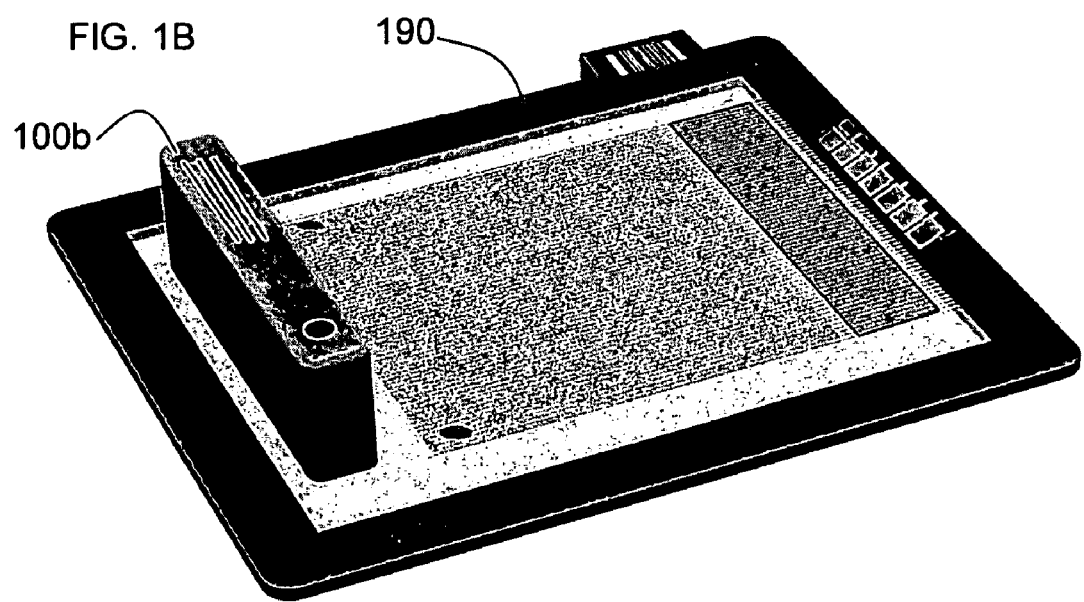
FIG. 1B illustrates a cartridge interfacing with a chip in accordance with at least one exemplary embodiment.

FIG. 1A illustrates a nonlimiting example of a cartridge 100a in accordance with at least one exemplary embodiment, and FIG. 1B illustrates the interaction between a cartridge 100b and a chip 190. The cartridge 100a illustrated in FIG. 1A includes: an external sample inlet 110; optionally an inlet cap 115; a sample chamber A; a push valve B1 that can be pushed to allow an external sample to enter the sample chamber A (e.g., which can be evacuated via a pump inlet F1, then sealed, to have a lower pressure to initiate an external sample to enter chamber A); optional electrodes 140 (e.g., to provide a voltage difference to break up cell membranes or cell walls to release the genomic material into or within chamber A); a push valve B2 that can be pushed to allow the genomic material from chamber A to enter a reaction chamber B; where binding and release substrates 150 can bind and release genomic material; where optional electrodes 160 can be used to direct the genomic material (e.g., genomic material extracted from the sample) into channel D, while waste material can be directed via channel C out through waste outlet I3; where a printhead 130 collects genomic material in a printhead chamber E and can be used to eject material into channels, e.g., microfluidic inline reaction channels, e.g., positioned flush with the cartridge (not shown); where wash can be inserted via a wash insertion inlet I1; where reagent can be inserted via a reagent insertion inlet I2; where a reagent insert valve can be pushed B3 to allow reagent to enter the reaction chamber B; where a wash insert valve can be pushed B4 to allow wash to enter the reaction chamber B; and where an optional power system 120 can supply the power to the printhead 130, and electrodes 140 and 160, and binding and release substrates 150. In at least one exemplary embodiment of the invention, the power system 120 supplies power to a thermal energy generator connected to or comprised within the printhead 130. In at least one exemplary embodiment of the invention, the path of released genomic material moving from reaction chamber B through channel D leading to printhead chamber E, along with the associated movement of the genomic material and associated electrodes 160 optionally controlling the movement of the genomic material, is referred to as a genomic separation and direction system.

Note that FIG. 1A illustrates only one nonlimiting example; variations are intended to lie within other exemplary embodiments. For example, the power system 120 can be external, the reagents and wash can lie in internal cambers in the cartridge, the push valves can be replaced with other types of methods to prohibit and allow fluid passage as known by one of ordinary skill in the relevant arts (including push valves and other devices or methods controlled by electronic means), the waste material can be stored in an internal chamber in the cartridge, and, although FIG. 1A illustrates genomic material from one sample being injected, multiple insertions from various samples from, e.g., different individuals (e.g., patients), or other sources (e.g., a water supply) can be inserted by, e.g., duplicating parts of the cartridge already described, e.g., one for each person (e.g., patient) or other source (e.g., a water supply) sampled.

Although there is no limitation to the amount of sample that can be collected into a cartridge of the invention, it is contemplated that the cartridge be used to determine genomic material from approximately 100 µl of sample. For example, volumes for preparation of a sample by a cartridge of at least one exemplary embodiment of the invention can be in the range of 10 µl to 1 ml.

In a cartridge of at least one exemplary embodiment of the invention, genomic material is isolated from a sample using only a homogeneous aqueous solution. Use of a homogeneous solution conveniently obviates the inefficient requirement of most methods of isolating genomic material (e.g., switching between alcohol-based or other organic-based solutions and aqueous solutions, and centrifugation), and also facilitates the use of the cartridge with the liquid ejection mechanism of exemplary embodiments of the present invention. Also unlike methods where genomic material is bound to a substrate, the cartridge of the present invention (incorporating the "charge switch" technology described herein) allows the genomic material to be bound to a substrate under one condition or released from the substrate under another condition. Thus, it is within the scope of the invention that a cartridge can, in some exemplary embodiments, be reused to isolate genomic material from more than one sample.

For example, in at least one exemplary embodiment, a sample can be collected, diluted to achieve a certain volume (e.g., in an aqueous lysis buffer), and simultaneously or subsequently drawn into a cartridge of the invention (e.g., into a reaction chamber of the cartridge), the conditions of which promote binding of the genomic material to the surface of a binding and release substrate (also referred to herein as substrate). In another exemplary embodiment, the aqueous lysis buffer can be diluted within the cartridge. After binding of the genomic material to the binding and release substrate, unbound macromolecules (e.g., proteins, contaminants, etc) are washed away. The condition of the cartridge can then be changed to release (i.e., elute) the genomic material into, e.g., an aqueous buffer solution or water. The eluate comprising genomic material can then be sent via a liquid ejection mechanism, as described herein, to a microfluidic chip for analysis. In at least one exemplary embodiment of the invention, the cartridge is disposed after it is used with a sample. In another exemplary embodiment of the invention, the cartridge can be washed, including subjecting the surface of a substrate of the cartridge to conditions that promote binding and/or release of genomic material, and reused to isolate genomic material from another sample.

For purposes of a cartridge of at least one exemplary embodiment of the invention, a binding and release substrate can be any suitable support with a solid surface, e.g., particles, beads, tubes, wells, glass, plastic, etc. A suitable support with a solid surface for a cartridge of at least one exemplary embodiment of the invention is such that it can have a natural affinity for genomic material or it has been or is easily conditioned (e.g., with conditioning buffer) for the binding and release of genomic material within the cartridge. Suitable methods for conditioning the surface of a solid-phase support include treating it with conditioning buffer (e.g., a substance that can introduce a charge (e.g., a positive charge) on the surface, or cause the surface to be hydrophilic or hydrophobic, etc.). Additionally, a suitable support can be magnetizable, magnetic, paramagnetic, etc. In at least one exemplary embodiment, the inner surface of the cartridge includes the inner surface of a channel(s) within the cartridge. In at least one further exemplary embodiment of the invention, the inner surface of the cartridge can be used as the substrate. In another exemplary embodiment, particles or beads (including magnetized or magnetizable particles or beads) within the cartridge can be used as the substrate.

For example, U.S. Published patent application Nos. 2003/0054395 and 2003/0130499, each of which are incorporated herein by reference in their entireties, describe methods of isolating genomic material in an aqueous solution comprising conditioning a solid phase substrate to bind and subsequently release genomic material. Briefly, these applications describe providing the surface of a solid phase substrate (e.g., a non-porous solid-phase substrate) with a charge that can be switched depending on the conditioning buffer, i.e., "charge switch material," that is in, on, or actually comprises the solid phase substrate. According to U.S. Published patent application No. 2003/0054395, charge switch materials are ionizable. For example, chemical species comprising ionizable groups can be immobilized onto solid supports in monomeric or polymeric form via adsorption, ionic or covalent bonds, or covalent attachment to a polymer backbone, which, in turn, is immobilized onto a solid support. Alternatively, chemical species can be incorporated into solid and insoluble forms, e.g., beads, particle, paths, channels, etc. (e.g., within a cartridge). The charge switch material is generally chosen so that the pKa of the ionizable group is appropriate to the conditions at which it is desired to bind and release nucleic acids from the solid phase substrate. Generally, genomic material will bind to the charge switch material at a pH below or roughly equal to the pKa, when the charge switch material is positively charged, and will be released at a higher pH (usually above the pKa), when the charge switch material is less positively charged, neutral, or negatively charged. In other words, in conditions of low pH, the substrate surface has a positive charge that is able to bind to negatively charged genomic material. Contaminants, e.g., proteins, other macromolecules, etc., are not bound and can be washed away in an aqueous wash buffer at normal physiological temperatures. Increasing the pH will neutralize the charge of the substrate surface and effect the release of genomic material, which can be eluted with an aqueous elution buffer.

Consequently, in at least one exemplary embodiment of the invention, the inner walls of the cartridge, or of a channel(s) within the cartridge, can be a solid phase substrate provided with a charge that can be switched depending on the condition of pH. In another exemplary embodiment, small solid phase particles or beads (e.g., magnetic beads) to which a switchable charge can be provided are within the cartridge. This latter exemplary embodiment provides an appropriate mechanism for preventing the beads from being washed away with the contaminants, e.g., by application of a magnetic field. In at least one exemplary embodiment, an optional power system within or external to the cartridge, supplies power to effect changes in the state of the binding and release substrate(s) of the invention.

Fluid (e.g., conditioning buffer, sample, lysis buffer, contaminants, eluate, wash buffer, etc.) can take different paths within the cartridge for the isolation of genomic material, and ultimately, the ejection of sample droplets that may contain isolated genomic material. For example, the sample can proceed along a straight, winding, or tubular path (which can be of any three-dimensional shape (e.g., a tube that is circular, semi-circular, square, etc. in cross-section)), join another path (e.g., to be mixed with lysis buffer), separate into two or more other paths within the cartridge, be allowed to pool, mix, and/or incubate with other materials, etc. In at least one exemplary embodiment of the invention, capillary action is used to draw the sample, conditioning buffer, lysis buffer, contaminants, eluate, wash buffer, etc., through the cartridge to a liquid ejection mechanism of at least one exemplary embodiment of the invention. Capillary action may require that the cartridge be filled with fluid (e.g., with conditioning buffer) prior to the introduction of the sample; in another exemplary embodiment, pressure from the injection of the sample (e.g., blood) can alone be sufficient to propel the sample through the cartridge. In a further exemplary embodiment of the invention, a vacuum is applied to draw the sample through the cartridge. In still another exemplary embodiment, electrokinetic forces move the sample, or portions of the sample (e.g., genomic material extracted from the sample), through the cartridge.

Another component of the cartridge is its ability to reduce the volume of the patient sample. In at least one exemplary embodiment of the invention, any isolated genomic material is eluted in a volume of liquid that is less than the original volume of the sample. In at least one further exemplary embodiment of the invention, any isolated genomic material is eluted in microliter, e.g., about 1-10 µl, e.g., about 2.5 µl, volumes.

As the methods herein describe DNA amplification processes, if the genomic material isolated is RNA, it must first be reverse transcribed into DNA, e.g., cDNA, prior to amplification via the microfluidic chip. Methods of reverse transcription are well known in the art. In at least one exemplary embodiment, the genomic material isolated is the entire genomic DNA of an organism. In another exemplary embodiment, genomic DNA is purified to the exclusion of RNA using well-known reagents, e.g., RNase.

A skilled artisan will recognize the desirability for isolation technology, e.g., wherein sample droplets are maintained separately from each other (e.g., a sample droplet is isolated and distinct from the sample droplet before it and the sample droplet after it), particularly for molecular diagnostics. Although most automated inline platforms utilize a sipper for such isolation, i.e., to draw a prepared sample into a microfluidic chip, use of a sipper is wasteful since the entire sample in the well is not examined. Additionally, sippers do not lend themselves well to massive sample partitioning, i.e., partitioning a sample with a small volume, e.g., about 2.5 µl, into, e.g., about one thousand isolated (sample) droplets. The present invention resolves the limitations of a sipper and facilitates massive sample partitioning via a liquid ejection mechanism. For example, a cartridge of at least one exemplary embodiment of the invention can be attached or connected in an airtight manner to a liquid ejection mechanism for ejecting sample droplets, including DNA sample droplets, by way of a liquid jet system that is adapted to eject sample droplets into, or across an airspace to be received by, a microfluidic inline reaction channel of a microfluidic chip.

B. Liquid Ejection Mechanism

As noted, a cartridge of at least one exemplary embodiment of the invention comprises, or is provided with a connection(s) to, a liquid ejection mechanism for ejecting sample droplets, including DNA sample droplets, by way of a liquid jet system. The liquid ejection mechanism in turn can comprise one or more liquid ejecting sections, i.e., an ejection head (also referred to herein as a printhead). The number of ejection heads is typically predetermined by the number of samples to be tested or the number of microfluidic inline reaction channels in a microfluidic chip. Each of the liquid ejecting (or liquid ejection) heads is provided with a liquid-containing reservoir section for containing a prepared sample, an ejection port fluidly communicating with the liquid reservoir section (if necessary, together with a liquid path for communicating the liquid reservoir section with the corresponding ejection port), and an energy-generating mechanism provided adjacent to the ejection port. This arrangement makes possible massive partitioning of the prepared sample by ejecting sample droplets independently of the prepared sample remaining in the liquid-containing section.

An ejection head of at least one exemplary embodiment of the invention is adapted to eject or expel sample droplets, typically utilizing thermal energy provided by a thermal energy generator. A conventional liquid jet system can be used, such as a bubble jet system that ejects liquid by generating bubbles (e.g., fluid bubbles) using thermal energy from electrothermal converters, such as heaters or lasers. In addition, in at least one exemplary embodiment of the invention, the ejector head is a piezo jet system. Thus, a conventional piezo jet system that ejects liquid by applying a voltage to the piezo-element can be utilized. The ejection head to be used with the thermal jet system has a relatively simple structure as compared with the head in the piezo jet system, and hence, can more easily be downsized and provided with a multi-nozzle. Additionally, the time required for forming the sample droplets for delivery to the microfluidic inline reaction channel (or port) is relatively short, so that production of a secondary structure of DNA by the heat can be avoided, and the efficiency of subsequent hybridization, e.g., to amplification primers, can be improved. Thus, the thermal jet system is advantageously used as the liquid jet system for the purpose of the present invention.

Typically, it is advantageous for the purpose of the invention to apply the basic principles in the field of liquid jet recording for projecting droplets of liquids (e.g., as disclosed in U.S. Pat. Nos. 4,723,129 and 4,740,796) to sample droplet ejection. Both disclosed principles of so-called on-demand type and continuous-type processes can be applied herein. However, it may be advantageous to use the on-demand type process for the purpose of this invention to minimize thermal energy generated in the electro-thermal converters arranged in correspondence to the liquid paths. Consequently, fluid bubbles can be formed in the prepared sample in one-to-one correspondence relative to the drive signal. A prepared sample(s) is ejected by way of an ejection port as a result of growth and contraction of the bubble to produce at least one sample droplet. If the drive signal is repetitive (e.g., 1 kHz to 100 kHz' e.g., 50 kHz), multiple picoliter drops can be dispensed in a short time frame to generate a fluid bubble of any practical size and volume needed for the particular analysis. Since the volume ratio of the fluid bubble to the encompassing medium can be controlled, known dilute concentrations can be achieved when dispensing sample droplets (e.g., sample droplets comprising genomic material and reagents). A pulse-shaped drive signal, as described in U.S. Pat. Nos. 4,463,359 and 4,345,262 can suitably be used for these purposes. In at least one exemplary embodiment of the molecular diagnostic device of the invention, the ejector head of the cartridge can be repetitively pulsed to form multiple droplets in sequence at a repetitive pulse rate to achieve a controlled total droplet volume in the microfluidic inline reaction channel of the microfluidic chip (e.g., in the microfluidic port of the microfluidic inline reaction channel). In at least one other exemplary embodiment of the invention, the repetitive pulse rate is in the range of about 1 kHz to about 100 kHz. In at least one further exemplary embodiment, the repetitive pulse rate is about 50 kHz. Ejections of sample droplets can be further improved when conducted under well-known conditions, e.g., as described in U.S. Pat. No. 4,313,124.

In at least one exemplary embodiment of the invention, an ejected sample droplet has a volume in the range of about 1 picoliter to about 25 picoliters. In at least one other exemplary embodiment, the volume of the ejected sample droplet is 3 picoliters. In at least one further exemplary embodiment of the invention, the total sample droplet volume (e.g., the summation of ejected sample droplets as received together in, e.g., the microfluidic port of a microfluidic inline reaction channel) is in the range of about 3 picoliters to about 100 nanoliters. In at least one additional exemplary embodiment of the invention, the total sample droplet volume is in the range of about 20 picoliters to about 10 nanoliters.

As for the configuration of the ejection head, those configurations taught by U.S. Pat. Nos. 4,558,333 and 4,459,600 are within the scope of the present invention. Additionally, the advantages of the present invention can be more effectively attained by providing a common slit for the ejection sections of a plurality of electro-thermal converters (as disclosed in Japanese Patent Application Laid-open No. 59-123670) and arranging an open hole for absorbing pressure waves (as disclosed in Japanese Patent Application Laid-open No. 59-138461). In short, regardless of the particular configuration of the liquid ejection head, capture of sample droplets by a microfluidic inline reaction channel can be accurately and efficiently realized according to the present invention.

Furthermore, a serial-type liquid ejection head rigidly secured to the apparatus main body, a replaceable tip-type liquid ejection head that is electrically connected to the apparatus main body, or a cartridge-type liquid ejection head provided with an integral solution reservoir can be advantageously utilized.

In at least one exemplary embodiment of the invention, a liquid ejection mechanism comprising a liquid ejection head that is provided with an ejection-restoring apparatus and/or a spare auxiliary apparatus is used. Specific examples include a cleaner to be used for the liquid ejection head, a pressurizing or suction device, a spare heater that can be an electro-thermal converter or a heating element of a different type or a combination thereof, and a spare ejector that is adapted to eject liquid in a form other than spotting.

Liquid jet systems generally generate waste in the form of satellite droplets that are smaller than the sample droplets. In at least one exemplary embodiment, these satellite droplets are angled away from any microfluidic inline reaction channel to prevent contamination. The airspace between any ejection head and any microfluidic inline reaction channel can be utilized to prevent contamination by satellite droplets by providing a vacuum or another suitable device to draw satellite droplets away from a microfluidic inline reaction channel and toward, e.g., any well-known and suitable waste capture mechanism. In addition, the waste capture mechanism can be used to capture waste from the cartridge, e.g., conditioning buffer, waste fluids from cleaning, etc.

In at least one exemplary embodiment, the design of the liquid ejection mechanism allows an ejection head and a microfluidic inline reaction channel to be aligned in a manner that facilitates ejection of sample droplets from the liquid ejection head across an airspace into a microfluidic inline reaction channel. For example, in at least one further exemplary embodiment, both the at least one microfluidic inline reaction channel and the at least one ejection head are in a fixed position relative to each other. However, the ejection head can still rotate to point in different directions, e.g., to point toward a waste capture device. Also, the microfluidic inline reaction channel can be designed to accept sample droplets from various angles (e.g., the entry to the microfluidic inline reaction channel can have a funnel-like opening) with plural ejection heads aimed at the channel entry. In such an exemplary embodiment(s), one or more sample droplet ejection heads can be placed at different angles in relation to the direction of the droplet movement from respectively attached cartridges (e.g., the various different angles allow more than one ejection head to supply sample droplets to a single microfluidic inline reaction channel). It is within the scope of the invention that at least one cartridge containing (prepared) patient samples to be tested comprises, or is attached to, its own ejection head, and that the ejection head is able to be aimed towards at least one microfluidic inline reaction channel(s).

Figure 2:
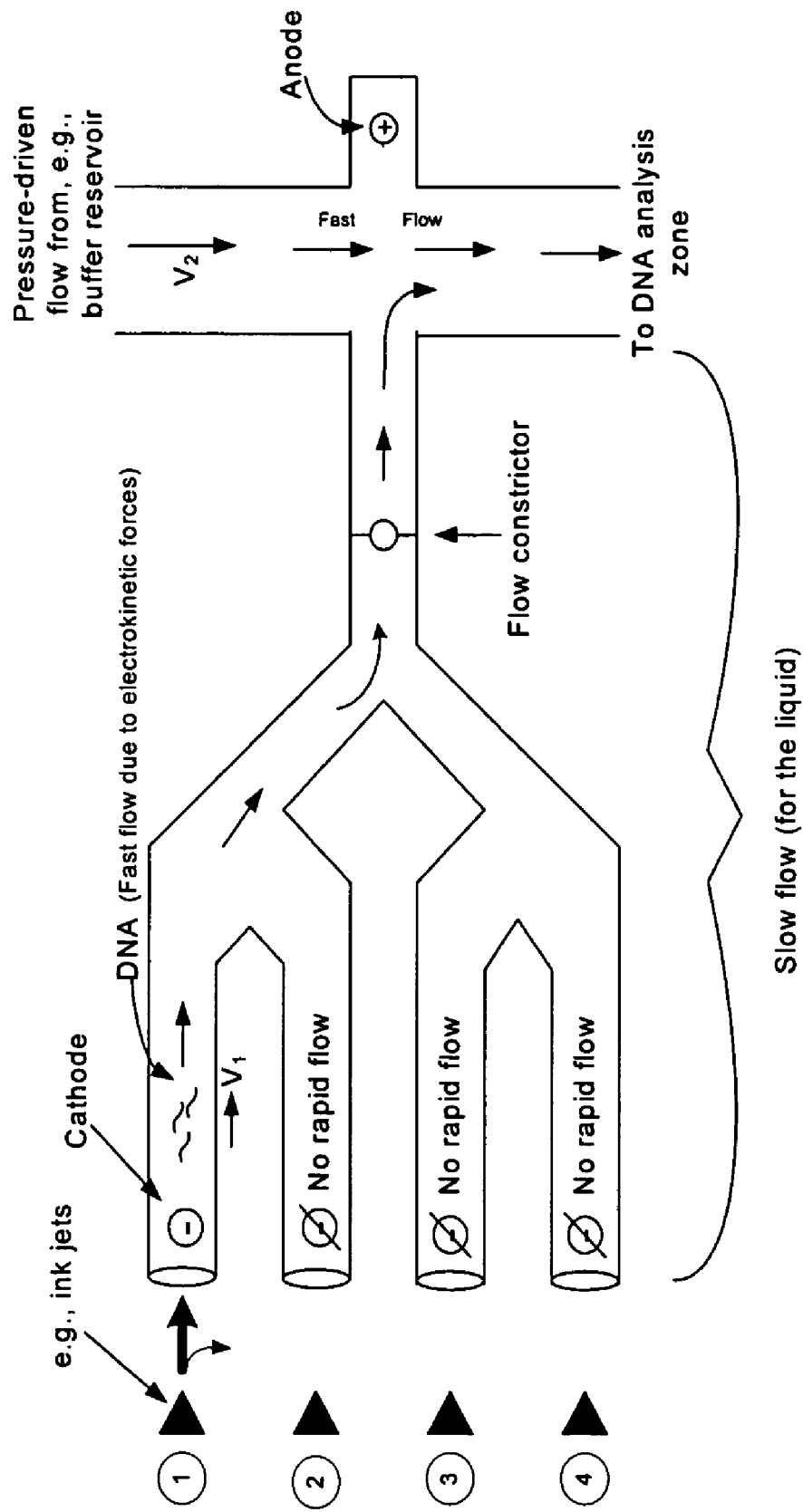
FIG. 2 schematically diagrams ejection heads and microfluidic ports in fixed positions relative to each other in accordance with at least one exemplary embodiment.

Alternatively, in at least one other exemplary embodiment wherein the at least one ejection head and at least one microfluidic inline reaction channel are in a fixed position relative to each other, there can be multiple ports leading to the microfluidic channel. In this exemplary embodiment, each multiple ejection head is desirably aligned to one of multiple microfluidic ports (e.g., as many as there are ejection heads). Each microfluidic port leads to a single microfluidic inline reaction channel (see, e.g., FIG. 2). In at least one further exemplary embodiment, one ejection head can move between cartridges containing (prepared) samples to be tested (or blank cartridges for purposes of cleaning the ejection head). After being attached to a cartridge, the ejection head can be angled toward at least one microfluidic inline reaction channel that is in a fixed position (or toward a waste capture mechanism when the attached cartridge is expelling waste (e.g., conditioning buffer) or when the attached cartridge is a cleaning cartridge). In another exemplary embodiment, one or more ejection heads can remain in a fixed position, and the microfluidic chip can move such that at least one microfluidic inline reaction channel aligns with different ejection heads at different positions.

In at least one exemplary embodiment of the invention, the cartridge comprises an ejection head(s) (e.g., a printhead(s)) of the invention (see, e.g., FIG. 1A). In at least one other exemplary embodiment of the invention, the cartridge, comprising the ejection head(s), is configured to deliver a sample comprising genomic material to the microfluidic chip, e.g., to the microfluidic port(s) of a microfluidic inline reaction channel(s) of the microfluidic chip. In at least one further exemplary embodiment, the sample comprising genomic material, as found in, e.g., the printhead chamber E and/or the expelled (or ejected) sample (or sample droplets) directed to, e.g., the microfluidic port, further comprises reagent(s), e.g., reagent(s) inserted into the cartridge via a reagent insertion inlet I2.

2. Amplifying Genomic Material and Detecting Amplified Products

As described above, after a sample is prepared and sample droplets are repeatedly ejected by a liquid ejection mechanism, the sample droplets, which can be approximately 1-25 pl (or some other appropriate volume) are analyzed with a microfluidic chip. In particular, a microfluidic inline reaction channel receives successive sample droplets of a sample (e.g., via a funnel and/or a microfluidic port), and sample droplets are analyzed via automated methods. The total sample droplet volume (e.g., the summation of ejected sample droplets as received together in, e.g., the microfluidic port of a microfluidic inline reaction channel) can have a volume in the range of about 3 picoliters to about 100 nanoliters. Analysis comprises mixing with amplification and/or detection reagents (in the reagent assembly area of the chip), amplifying the genomic material (in the amplification area of the chip) and detecting amplified products (in the detection area of the chip), and/or mapping the genomic material (in the matrix analysis area of the chip).

A. Microfluidic Port

Sample droplets can be ejected directly into a microfluidic inline reaction channel. Additionally, it is within the scope of the invention that sample droplets be ejected into at least one microfluidic port, comprising an entry and a channel, and which leads to a microfluidic inline reaction channel (see, e.g., FIG. 2). In this exemplary embodiment of the invention, a sample droplet can be ejected toward the entry of the microfluidic port, which is suitably sized to receive the ejected sample droplet (e.g., is appreciably larger than the ejected sample droplet), the microfluidic port channel, and/or the microfluidic reaction channel, etc., each of which can conveniently have a funnel shape. In at least one exemplary embodiment of the invention, a sample droplet receiving system, e.g., a microfluidic inline reaction channel and/or a microfluidic port leading to a microfluidic inline reaction channel, is configured to receive at least a portion of sample droplets comprising genomic material ejected by an ejector head, e.g., an ejector head contained within a cartridge. In at least one other exemplary embodiment of the invention, the entry of the port is ten times the size of a microfluidic port channel. In at least one further exemplary embodiment of the invention, the widest diameter of the entry to the microfluidic port is, e.g., 1 mm, and the diameter of the port channel, is, e.g., 100 µm.

Sample droplets can be transported through the port channel based on the negative charge of the genomic material, i.e., electrokinetically, and/or with a pressure-driven flow. In at least one exemplary embodiment of the invention, the movement of a sample droplet within the port channel is entirely, or in large part, controlled electrokinetically (e.g., by pairs of cathodes and anodes). For example, a cathode can conveniently be placed at the entry of each microfluidic port and an anode placed at the other terminus of each port channel (e.g., within the microfluidic inline reaction channel to which the port channel leads (see, e.g., FIG. 2)). To control the flow of fluid in each port if there are multiple microfluidic ports, and consequently, multiple pairings of cathodes and anodes, each pairing controlling the fluid movement within a particular microfluidic port can be activated only after the particular microfluidic port has received one or more sample droplet(s) of a sample. It is also within the scope of this exemplary embodiment that a sample droplet is transported into and through a microfluidic inline reaction channel via a pressure driven flow. Additionally, transport of a sample droplet through a port channel into a microfluidic inline reaction channel can be controlled via the use of well-known flow constrictors.

Other well-known forces, e.g., surface tension, can be used to drive a sample droplet through a microfluidic port, channel, and/or inline reaction channel. For example, in at least one exemplary embodiment of the invention, a microfluidic port entry, channel, and/or inline reaction channel can be filled with a buffer, e.g., the same buffer as the eluate comprising genomic material, that promotes a collection of sample droplets at the microfluidic port entry via, e.g., surface tension forces. In this exemplary embodiment, it may be observed that a sample droplet becomes part of the buffer, and does not remain a discrete droplet. However, the electro-osmotic component of electrokinetic force creates a uniform pluglike flow of fluid down a channel, reducing or preventing diffusion of genomic material. Consequently, as used herein, sample droplet and sample plug (including DNA sample droplet and DNA sample plug) refer to the plug-like cross-section of the continuous flow of fluid comprising the sample ejected as a sample droplet from the ejection head as the cross-section progresses through a microfluidic port channel into a microfluidic inline reaction channel. Similarly, as described herein, a "primer plug" refers to the cross-section at any time of a continuous flow of liquid comprising a particular "plug" of amplification and/or detection reagents.

B. Microfluidic Inline Reaction Channel

Generally, as described above, a microfluidic inline reaction channel can contain, e.g., a water-based liquid that provides the basis for the sample liquid. Alternatively, the microfluidic inline reaction channel liquid can be an organic-based liquid, for example, silicon oil of about 60 poise. In at least one exemplary embodiment of the invention, repetitive sample droplets are ejected into a microfluidic inline reaction channel and spacers separate the sample droplets. In at least one other exemplary embodiment, air separates the sample droplets. In at least one further exemplary embodiment, a hydrophobic substance, such as mineral oil, or some other organic-based liquid or solvent or the like, is used as a buffer spacer between each sample droplet in order to surround and separate each sample droplet from the preceding or following sample droplet in the microfluidic inline reaction channel. In addition, the inner wall of the microfluidic channels of a molecular diagnostic device of at least one exemplary embodiment of the invention can be provided with a hydrophobic coating to decrease or prevent cross-contamination between sample droplets. In at least one other exemplary embodiment, as described above, the electro-osmotic component of the electrokinetic force producing movement of the, e.g., sample plug (e.g., DNA sample plug) prevents or reduces diffusion of genomic material in the plug. In other words, despite the movement inherent in microfluidics, the hydrophobic/hydrophilic difference between the microfluidic inline reaction channel liquid and the buffer spacers (e.g., oil or air) enables a single DNA molecule to be kept in the plug (e.g., DNA sample plug) during its movement along a microfluidic inline reaction channel without mixing with the buffer space, or with adjacent droplets or plugs.

Generally, a microfluidic inline reaction channel of a microfluidic chip can be 50 µm to 300 µm in diameter, and is typically 100 µm in diameter. As with the microfluidic port channel, a microfluidic inline reaction channel can be a tube that is spherical, hemispherical, square, etc., and formed in glass, quartz, plastic, etc. and can be formed of different materials depending on the area of the chip, e.g., can be formed with transparent material when it is within the detection area of a molecular diagnostic device. Methods of forming microfluidic inline reaction channels in a microfluidic chip are well known in the art. A microfluidic inline reaction channel can have any desired configuration, e.g., it can be straight, can form a joint or union with another microfluidic inline reaction channel at a confluent junction, can separate into two or more microfluidic inline reaction channels at a separate junction, can allow the fluid within it to pool and/or mix, etc. Also, as described above, the flow within a microfluidic inline reaction channel can be controlled by, e.g., electrokinetic forces, hydrodynamics (i.e., pressure), or a hybrid of the two.

Figure 3:
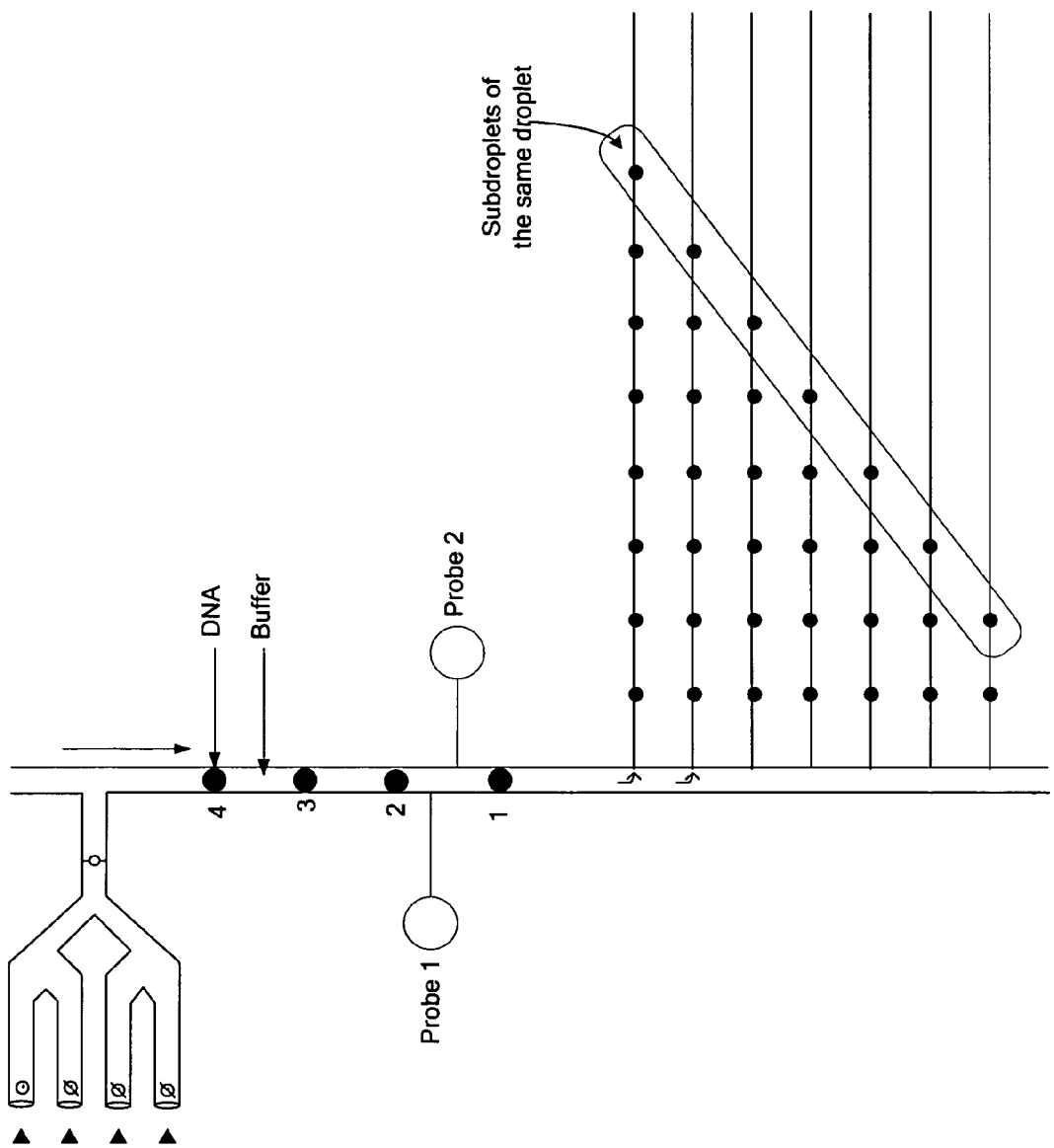
FIG. 3 schematically diagrams a massive sample partitioning of a microfluidic inline reaction channel into multiple subchannels in accordance with at least one exemplary embodiment.

In at least one exemplary embodiment of the invention, a "parent" microfluidic inline reaction channel can also be used for massive sample partitioning. For example, a microfluidic inline reaction channel can lead into more than one "subchannels," each of which can have, e.g., one-tenth the flow rate of the parent microfluidic inline reaction channel (see, e.g., FIG. 3). This structure facilitates the partitioning of each sample droplet into "subdroplets," e.g., if a parent microfluidic inline reaction channel leads to ten subchannels, each with one-tenth the flow rate of the parent microfluidic inline reaction channel, then each droplet will be divided into ten subdroplets, each in its own subchannel. This partitioning, especially when repeated, is referred to herein as an embodiment of massive sample partitioning. For purposes herein, a microfluidic inline reaction channel encompasses such subchannels and a sample droplet encompasses such subdroplets. Additionally, the parent microfluidic inline reaction channel can be tapered to effect the desired partitioning. Additionally, this method of massive sample partitioning can occur 1) prior to and/or after the reagent assembly area of the chip, 2) prior to and/or after the amplification area of the chip, 3) prior to and/or after the detection area of the chip, and/or 4) prior to or within the matrix analysis area of the chip. A microfluidic inline reaction channel (or subchannel) can be confluent with other microfluidic inline reaction channels, e.g., for the addition of amplification and/or detection reagents, e.g., primer plugs.

C. Reagent Assembly/Amplification Area

Figure 4:
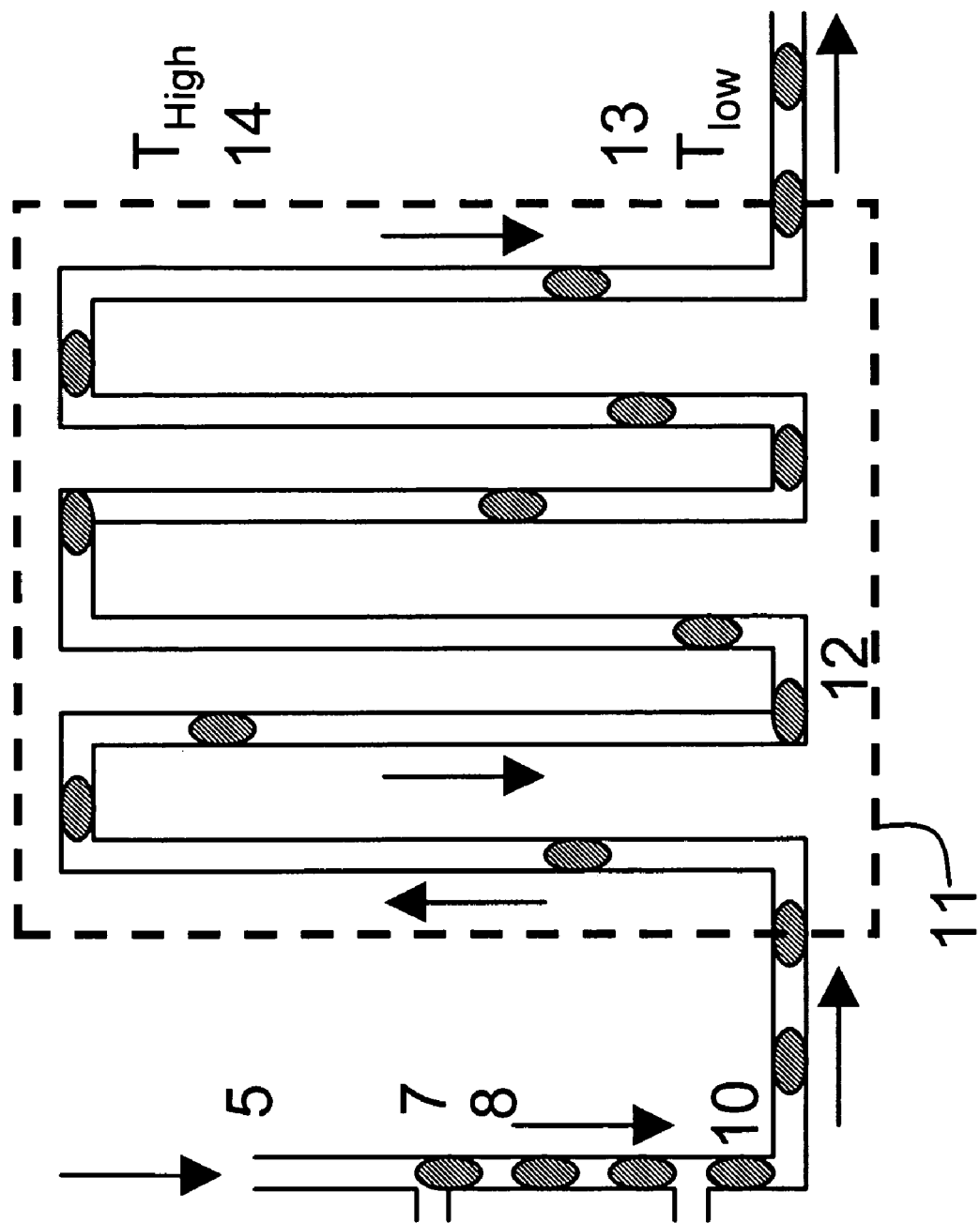
FIG. 4 schematically delineates a sample droplet path as it is mixed with amplification reagents to form a sample plug in the reagent assembly area and is amplified within the amplification area in accordance with at least one exemplary embodiment.

FIG. 4 provides a nonlimiting example of a reagent assembly and amplification area of a microfluidic chip that comprises one microfluidic inline reaction channel. Of course, multiple microfluidic inline reaction channels and/or subchannels that run parallel to each other are within the scope of the invention. In the microfluidic chip, each sample droplet (8) that is in a microfluidic inline reaction channel (5) is further prepared at, e.g., a junction (10), e.g., a T-shaped junction, to form a sample plug by being mixed with a primer plug comprising amplification reagents (e.g., primer(s), nucleotides, polymerase, etc.) and optionally detection reagents (e.g., detectable agents, e.g., labels, fluorescent probes, intercalators, etc.). A skilled artisan will recognize which amplification reagents should be mixed with each sample droplet and at what concentrations the reagents should be used. For example, amplification reagents typically include a polymerase, dNTPs, magnesium, buffer, and a primer or a pair of primers. One of skill in the art will also be able to determine the primer or primer pair to be used; e.g., if PCR is performed, a primer pair would be appropriate. In contrast, if waveform-profiling analysis is performed, a waveform primer would be appropriate. The design and selection of such primers are known in the art. Additionally, detection reagents and methods of using such reagents to directly or indirectly label amplified DNA products are well known.

After a sample droplet has been ejected into a microfluidic port (or microfluidic inline reaction channel), and mixed with amplification reagents to form a sample plug, it is transported along the microfluidic inline reaction channel into an amplification area of a device of at least one exemplary embodiment of the invention, i.e., a first temperature-controlled area. As the terminology is utilized herein, similar to a sample droplet, a sample plug may or may not comprise genomic material, and is considered a DNA sample plug if it does comprise genomic material.

As sample plugs (which comprise sample droplets combined with primer(s), e.g., primer plugs) are continuously drawn along an inline microfluidic reaction channel (5), they are introduced to an amplification area, i.e., a first temperature-controlled area, such as a thermal control plate (11). The path (12) of the microfluidic inline reaction channel can be such that it facilitates the movement of each sample plug in a winding and reciprocated manner between low temperature areas (13) and high temperature areas (14) of the thermal control plate (11).

A skilled artisan will recognize that (A) the temperatures of the low temperature areas (13), the high temperature areas (14), and areas between the low and high temperature areas, (B) the path (12) of a microfluidic inline reaction channel, and (C) the speed with which a sample plug moves though a microfluidic inline reaction channel, can be appropriately adjusted according to the chosen amplification method. For example, the low temperature area (13) can be set to a temperature appropriate to effectuate annealing and the high temperature area (14) can be set to a temperature to effectuate denaturing. Additionally, in at least one exemplary embodiment of the invention, the path (12) of a microfluidic inline reaction channel is designed to facilitate the movement of a sample plug in a reciprocated manner between the low temperature and high temperature areas to effectuate, e.g., approximately 20 to 40 cycles of denaturation, annealing, and elongation. Finally, the speed with which a sample plug (or DNA sample plug) flows through a microfluidic inline reaction channel can be set to allow each sample plug (or DNA sample plug) to remain at a denaturing, annealing, or elongating temperature for an appropriate length of time.

As previously described, each microfluidic inline reaction channel, or portions thereof, can also be rapidly heated and cooled in a localized and/or repeated manner such that the denaturing, annealing, and elongation steps of an amplification method (e.g., PCR, waveform profiling), are executed as a sample plug moves along a microfluidic inline reaction channel and through a first temperature-controlled area of a device of at least one exemplary embodiment of the invention. For example, Joule heating can be used to apply voltage to metal traces alongside, inside, and/or crisscrossed with each microfluidic inline reaction channel of a device of at least one exemplary embodiment of the invention. Alternative methods of heating microfluidic inline reaction channels include hot water, air, etc. Additionally, cooling of a microfluidic inline reaction channel, or portions thereof, can be achieved through the use of cooling fluid that travels through a coil to carry away thermal energy, or by facilitating rapid heat dissipation. Various methods of heating and cooling microfluidic inline reaction channels and the like are well known.

The temperatures, the length of time at such temperatures, and the number of cycles to which a DNA sample plug are subjected vary as desired to effectuate amplification of DNA for screening, identification, quantification, etc. For example, in at least one exemplary embodiment, denaturing temperatures are between 90° C. and 95° C., annealing temperatures are between 55° C. and 65° C., and elongation temperatures are dependent on the polymerase chosen (e.g., the optimal elongation temperature is about 72° C. for Taq polymerase). Also, the amplification method can comprise "hot starts" and/or a final incubation of a DNA sample plug at 75° C.

A sample plug can be moved through a microfluidic inline reaction channel at different speeds ranging between about 50 µm per second and about 5000 µm per second, e.g., about 500 µm per second. Varying the speed with which a sample plug moves through a microfluidic inline reaction channel can effectuate the duration of time a sample plug remains at a certain temperature (e.g., temperatures required for denaturing, annealing, elongation, etc.) depending on the volume of the reaction, the concentration of the genomic DNA, etc. For example, a typical cycling profile is approximately 94° for 1 min., 60° for 1 min., 72° for 1 min. (a typical rule for a 72° C. elongation is 1 min for each 1000 base pairs being amplified). In addition, the number of amplification cycles required can determine the appropriate path required of a microfluidic inline reaction channel.

After a sample droplet has been prepared, received by a microfluidic inline reaction channel, mixed with amplification reagents to form sample plugs, and the DNA within DNA sample plugs has been amplified, each sample plug is driven along the microfluidic inline reaction channel into a detection area of the device, which can also be a second temperature-controlled area. As described above, a sample droplet can undergo massive sample partitioning in a microfluidic inline reaction channel (i.e., in addition to massive sample partitioning via a liquid ejection mechanism) at any time after being received by a microfluidic inline reaction channel and before being drawn into the detection area of the microfluidic chip. A skilled artisan will recognize that only DNA sample plugs will comprise detectable amplified DNA products.

D. Detection Area

A molecular diagnostic device of at least one exemplary embodiment of the invention is designed to (A) allow DNA to be received as a sample droplet(s) by a microfluidic inline reaction channel, (B) form sample plugs in a reagent assembly area by mixing sample droplets with primer plugs comprising amplification reaction components and/or detection components, (C) effectuate the amplification of DNA as a DNA sample plug is advanced along the microfluidic inline reaction channel through an amplification area, i.e., a first temperature-controlled area, and (D) facilitate the detection of amplified DNA products as the DNA sample plug passes through the detection area.

Passing a microfluidic inline reaction channel through a detection area within a second temperature-controlled area is within the scope of the invention. Placement of a microfluidic inline reaction channel through the detection area within a second temperature-controlled area will subject sample plugs traveling along the microfluidic inline reaction channel to a temperature or temperature gradient (or sweep), i.e., one or more temperatures, during detection. One of skill in the art will recognize that detecting sample plugs as they are subject to a temperature sweep, e.g., detecting the fluorescence of a DNA sample plug at different temperatures, facilitates melting temperature analysis of, e.g., amplified DNA products.

Figure 5:
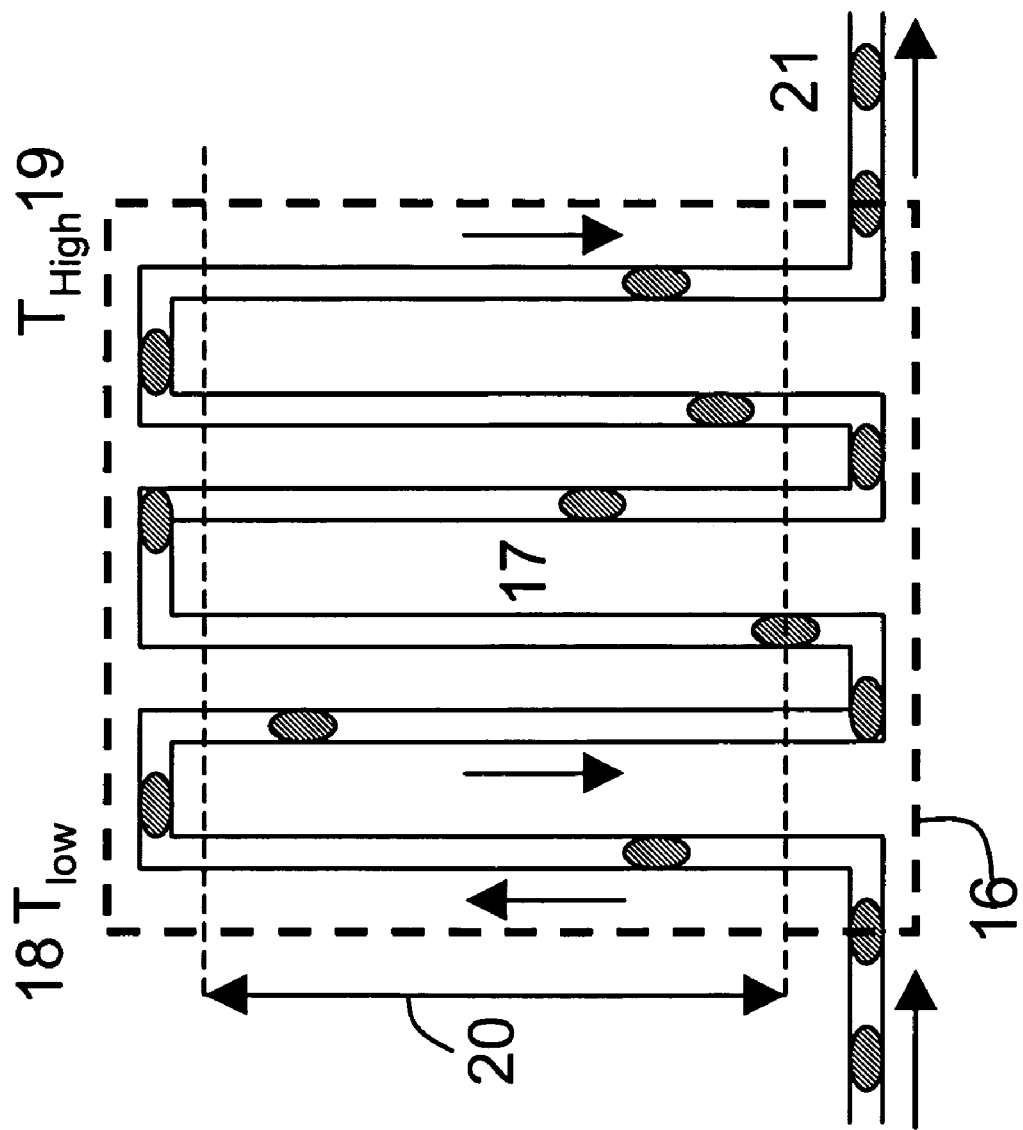
FIG. 5 schematically delineates a sample plug path in a microfluidic inline reaction channel after it has passed the temperature-controlled area of FIG. 4 and passes through a detection area in accordance with at least one exemplary embodiment.

FIG. 5 provides a nonlimiting example of a detection area of a microfluidic chip of at least one exemplary embodiment of the invention. As a sample plug is drawn along a microfluidic inline reaction channel (5, as in FIG. 4) and exits the first temperature-controlled area (e.g., 11, as in FIG. 3), it proceeds downstream to areas related to identification and/or analysis, e.g., it is introduced into a detection area, i.e., a second temperature-controlled area, which can be, e.g., a second thermal control plate (16). A microfluidic inline reaction channel can have a detection path (17) that facilitates the detection of the absence or the presence of amplified DNA in sample plugs, as the sample plugs move between lower temperature areas (18) and higher temperature areas (19). As sample plugs traverse through an optical scanning area (20), any detectable reagent (e.g., fluorescent probes, intercalators, etc.) can be optically excited, e.g., with three-color laser beams, and any resulting emissions can be measured.

Generally, the lower temperature areas (18) of the detection area can be set to temperatures ranging between about 25° C. to about 65° C. The higher temperature areas (19) of the detection area can be set to temperatures ranging between about 55° C. to about 95° C. In the case that PCR-amplified DNA is to be detected, the lower temperature areas (18) and higher temperature areas (19) of the detection area (16) can be set to one temperature, e.g., between about 25° C. to about 55° C.

The various instruments that can be used to regulate the temperatures in the detection area, excite detectable reagents in DNA sample plugs, and detect emissions, or a change in emissions, are commercially available. For example, temperature can be measured with, e.g., an infrared charge-coupled device (CCD) (not shown) covering the optical scanning area (20), or a larger or smaller scanning area. In at least one exemplary embodiment, placement of precise temperature sensors on the second thermal control plate to calibrate the infrared CCD is recommended to increase the accuracy of temperature measurements.

Subjecting a DNA sample plug to a temperature gradient or sweep in the detection area enables detecting a waveform profile produced by waveform profiling. As sample plugs traverse between temperatures, resulting emissions can be correlated with the temperature of a sample plug. Additionally, PCR-amplified DNA can be subjected to a temperature gradient, although the emissions need only be detected at one temperature. Alternatively, the lower temperature areas and higher temperature areas can be set to one temperature for the detection of PCR-amplified DNA.

The detection stage optical system (not shown) can be used to detect the change in emissions from amplified DNA, e.g., higher-order structures, as the amplified DNA is subject to a temperature sweep, by measuring, detecting, and determining the waveform profile of isolated DNA. Detection of a certain waveform profile can indicate that the screened sample is contaminated (e.g., with bacteria), and subsequent comparison of the resulting waveform profile with a database of waveform profiles produced with a known primer(s) and DNA isolated from a known organism(s) can identify the contaminating organism. Additionally, if isolated genomic material was concentrated within the sample liquid, and the concentration known, the level of contamination can be quantified upon detection of the waveform profile.

A device of at least one exemplary embodiment of the invention can be effectively utilized when little or no information is available regarding whether a sample is contaminated and/or what organism is contaminating a sample. Of course, the identity of an organism obtained from a waveform profile can be further confirmed using the present invention to provide PCR product(s) for analysis. In at least one exemplary embodiment of the invention, the identification of the organism is further narrowed by forming several DNA sample droplets from the same organism, combining each DNA sample plug with a different primer chosen specifically to confirm the identity of an organism, amplifying each DNA sample droplet with a different primer (or set of primers) by, e.g., PCR or processes related to waveform profiling, and detecting the absence or presence of amplified products. Correlating the presence of amplified products with the particular primer(s) used can provide the identity of the organism.

As described above, screening for the presence of an organism, identifying the organism, and/or quantifying the concentration of the organism in a sample can be performed via waveform profiling and/or PCR using a molecular diagnostic device of at least one exemplary embodiment of the invention comprising 1) at least one cartridge for extracting genomic material, etc., 2) at least one sample droplet ejection head, wherein at least one cartridge comprises, or can be attached to, at least one sample droplet ejection head for ejecting the genomic material; and 3) at least one microfluidic chip for analyzing the genomic material, wherein the microfluidic chip comprises at least one microfluidic inline reaction channel for receiving the ejected genomic material from the sample droplet ejection head and at least one metal trace or other component for heating of and/or fluid movement within the microfluidic inline reaction channel, and wherein the at least one microfluidic inline reaction channel runs through a reagent assembly area, an amplification area within a first temperature-controlled area for the amplification of DNA products, and a detection area. When a more detailed examination of isolated genomic material is required, a molecular diagnostic device of at least one exemplary embodiment of the invention can be used to select one or more DNA sample droplets, or DNA sample plugs (which may or may not have been amplified) from a sample of interest for mapping within the matrix analysis area of a microfluidic chip of at least one exemplary embodiment of the invention; in at least one exemplary embodiment, the DNA in the sample droplet or plug has not been amplified. As described above, a sample droplet can undergo massive sample partitioning in a microfluidic inline reaction channel (e.g., in addition to massive sample partitioning via a liquid ejection mechanism) at any time after being received by a microfluidic inline reaction channel, including before or after being drawn into the matrix analysis area of the chip.

3. Mapping of Genomic Material

The present invention can map the genomic information present in a DNA sample. Such mapping is contemplated to occur either (1) as a result of a need or desire for more information in response to partial characterization of the contaminating organism (e.g., genus, species) by use of the detecting steps outlined above, or (2) as a method of characterizing contaminating organisms independent of utilization of the detecting steps outlined above. Such mapping is further contemplated to occur within the matrix analysis area of the chip of at least one exemplary embodiment of the invention device. The mapping strategy improves upon the recently reported technology known as direct linear analysis ("DLA"; see Chan et al. (2004) "DNA mapping using microfluidic stretching and single-molecule detection of fluorescent site-specific tags" *Genome Res.* 14(6):1137-46, incorporated herein by reference in its entirety).

In at least one exemplary embodiment of the invention, in response to detection of bacterial DNA (or some other form of genomic DNA that is being monitored in the detection area of the chip), a series of sample droplets, e.g., a fresh series of sample droplets is produced by the liquid ejection head(s), as described above, and directed through at least one microfluidic inline reaction channel leading to the matrix analysis area of the chip. Dyes (intercalating and/or other dyes) are added to the sample droplets to form sample plugs, either before or within the matrix analysis area.

The matrix is an integral part of the matrix analysis area of the chip. The matrix is formed on, and contained within, a glass substrate that contains several microfluidic inline reaction channels for movement of microfluidic sample droplets through the units of the matrix analysis area. Each unit (or "pixel") of the matrix analysis area in turn comprises at least three components described herein. Each unit of the matrix analysis area is capable of (1) isolating and "stretching" molecules of DNA through the microchannel of a microfluidic DNA-stretching microchip; (2) generating beams of photons of visible light at more than one wavelength for exciting more than one dye bound to the molecules of DNA; and (3) detecting the results of the interaction of the beams of photons with the dyes.

In at least one exemplary embodiment of the invention, each sample droplet combines with a droplet (or plug) containing reagent(s) necessary for analysis. For this purpose a microfluidic inline reaction channel can be confluent with other microfluidic inline reaction channels, e.g., for the addition of the dyes and/or other reagents necessary for analysis in the matrix analysis area. In at least one further exemplary embodiment of the invention, the reagents include at least two dyes that will bind to the DNA present in the droplets. One of the dyes is nonspecific and binds (or intercalates) with the DNA in a nonspecific fashion (i.e., the DNA will be uniformly stained with intercalator) (see, e.g., Chan et al. (2004) *Genome Res.* 14(6):1137-46); the other dye is site-specific; for example, fluorescent peptide nucleic acids (PNAs) targeting, e.g., specific 7-8 bp sites (see, e.g., Chan et al. (2004)).

As described above (regarding the detection area of the chip), the distribution of droplets to the several units of the matrix analysis area can be accomplished by massive sample partitioning. The parent microfluidic inline reaction channel can be tapered to effect the desired partitioning. For purposes of rapidly and evenly distributing the sample droplets (and subdroplets) to the appropriate locations within the matrix analysis area, (1) the number of subchannels branching from a parent channel may be any number that can be accommodated within a device of at least one exemplary embodiment of the invention (i.e., 10, 100, 250, 500, 1000, or more), and (2) subchannels can branch from other subchannels. In at least one exemplary embodiment, subchannels branch from only other larger subchannels. In at least one further exemplary embodiment, 512 subchannels directly or indirectly branch from each of 512 larger subchannels, which in turn branch from a parent channel(s). In addition, this massive sample partitioning can occur prior to or within the matrix detection area of the chip. A microfluidic inline reaction channel(s) or subchannel(s) can be confluent with other microfluidic inline reaction channel(s) or subchannels, e.g., for the addition of dyes and/or other reagents necessary for the analysis steps of the matrix analysis area by DLA technology.

In at least one exemplary embodiment of the invention, through a series of microfluidic inline reaction channels (parent channel(s), and subchannels branching therefrom, and (optionally) smaller subchannels in turn branching therefrom), the matrix in the matrix analysis area comprises a 512×512 matrix, therefore comprising approximately 260,000 (e.g., 262,144) units (or pixels) for analysis of DNA molecules by the DLA technology. In at least one further exemplary embodiment of the invention, the matrix can be 2×2, 3×3, 9×10, 10×10, 100×100, 256×256, 1024×1024, or any appropriate square or nonsquare dimension.

The sample droplets or subdroplets can move through the channels and subchannels of the device of at least one exemplary embodiment of the invention by any number of means, and a predetermined rate(s) of movement of the droplets can be controlled by such means. For example, positive pressure applied to the beginning portion of a channel(s) or subchannel(s) and/or negative pressure (i.e., a vacuum) applied to an end portion of a channel(s) or subchannel(s) or to a waste well or the like can be utilized to move the droplets or subdroplets. In addition, electrokinetic forces can be used to move the droplets and subdroplets, as well as any other means known to one of skill in the art.

In at least one exemplary embodiment, the sample plugs, already combined with droplets containing reagent(s), proceed to a series of microfluidic inline reaction channels or subchannels that split off from the parent microfluidic inline reaction channel. A splitting device ("splitter") controls the flow of droplets along the various microfluidic inline reaction channels or subchannels in the series. For example, in a nonlimiting example of a 3×3 matrix, three channels are able to receive sample droplets from the splitter.

In this exemplary embodiment, a series of droplets or plugs moves along the parent microfluidic inline reaction channel toward the splitter. Distal to the splitter are three channels (herein numbered 1, 2, and 3), each attached to a vacuum for pulling the droplets along the microfluidic inline reaction channel. The first nine droplets (numbered 1-9) are treated in the following fashion. The splitter allows droplets to move into channel 1 (by means of the vacuum attached to channel 1) and droplets 1, 2 and 3 move along that channel until they are each situated in a predetermined location. The vacuum to channel 1 is then released or removed, and then the vacuum cycle for channel 2 commences (i.e., the vacuum is applied to channel 2, moving droplets 4, 5, and 6 into predetermined locations along channel 2). The procedure is then repeated for channel 3.

This procedure can be extended to any number of channels. In at least one exemplary embodiment of the invention, 512 channels are utilized, and 512 droplets move along each channel until each droplet is situated in a predetermined location. Thus a matrix alignment of 512×512 droplets is present in the device at the end of the vacuum cycle for channel 512.

In the aforementioned 3×3 matrix exemplary embodiment, at the end of the vacuum cycle for channel 3, nine droplets are located in predetermined locations on the matrix. At each of these predetermined locations is an entry port to a "unit" (or "pixel") of at least one exemplary embodiment of the invention. Thus, in a 3×3 matrix, there are nine (9) units of at least one exemplary embodiment of the invention. A unit of at least one exemplary embodiment of the invention, regardless of the number of units, comprises three main components. One component comprises a light source (e.g., a photon generator). A second component comprises a microfluidic DNA-stretching microchip (see Chan et al. (2004)) or similar structure using direct linear analysis (DLA) technology. A third component comprises a light detector (e.g., a photon detector).

Generally, there are several available forms of light sources and detectors (i.e., active optics devices). In addition, there are several available forms of passive optics, such as planar waveguides, microlenses, and filters, that can be used in combination with the active optics. For reviews related to the use of various forms of optics in microfluidic devices, see, e.g., Mogensen et al. (2004) *Electrophoresis* 25:3498-512; Sia and Whitesides (2003) *Electrophoresis* 24:3563-76.

Among the light sources and detectors known to be useful in microfluidic devices are light emitting diodes (LEDs), including organic light emitting diodes (OLEDs) (e.g., the combinations of an LED with a single-mode planar waveguide, a Si photodetector, and a microfluidic channel cast in poly(dimethylsiloxane) (PDMS) is known in the art, as is the integration of an LED, Si photodetectors, and microfluidic channels by means of conventional complementary metal oxide silicon (CMOS) processing and sacrificial underetching). In at least one exemplary embodiment of the invention, the light source (e.g., a photon generator) is also referred to as an emitter layer.

Lasers are also used in microfluidic devices. Vertical cavity surface emitting lasers (VCSELs) have been applied for near-infrared fluorescence detection of fluorophores spun onto a poly-(methyl methacrylate) (PMMA) substrate, in which the fabrication of the substrate also included a high pass filter and a photodiode for detection. In at least one exemplary embodiment of the invention, a filter is also referred to as a filter layer, and a light detector (e.g., a photon detector, e.g., a photodiode) is also referred to as a detector layer.

Another useful light source is a microdischarge light source, e.g., consisting of a metal anode and a microfluidic cathode filled with an aqueous solution of $BaCl_2$ (which was used for excitation of DNA molecules labeled with SYBR fluorophores).

Photodetectors for microfluidic systems (e.g., semiconductor photodetectors) include systems in which the photodiodes or the like were fabricated in the same substrate as a portion of the microfluidic channels (e.g., in a device for DNA analysis, an interference filter can be incorporated for suppression of excitation light). In another photodetector system, a commercially available CMOS imager chip was bonded to a microfluidic channel network cast in PDMS (measurements of bromophenol blue and Orange G were possible, as was fluorescence measurements, because the CMOS imager incorporated an interference filter). Another known technique involves the use of low-temperature thinfilm deposition techniques for production of amorphous silicon photodiodes with filters on top of glass substrates (as opposed to integration of the diode within a semiconductor wafer).

The integration of microlenses and planar waveguides in microfluidic devices typically improves detection, e.g., by focusing the light in the channel to increase the excitation power for fluorescence measurements, or by increasing the optical path length for absorbance detection using planar waveguides. A further advantage of planar waveguides is that beam splitting can be accomplished for multi-point detection; thus very compact devices can be realized when integrated with appropriate light sources and photodetectors. Microlenses can be fabricated on top of the substrate (to shape the light in a path perpendicular to a wafer) or fabricated in the plane of the device. 2D planar microlenses can also be employed in fabricating microfluidic devices. Planar waveguides (e.g., polymer waveguides, glass waveguides, photonic bandgap sensors, etc.) can also be useful in designing microfluidic devices. Of particular interest are photonic crystal structures: a photonic crystal can be viewed as the optical equivalent of a semiconductor crystal, and is characterized by a bandgap where light of a certain range of wavelengths is not allowed to be transmitted. Further information regarding optical systems for microfluidic devices is available in the literature (e.g., Mogensen et al., supra).

The light source (e.g., photon generator) and photodetector of at least one exemplary embodiment of the invention, along with the DNA-stretching microchip, are disclosed in more detail below.

A. Photon Generator

The photon generator component ("PGC"), e.g., in the emitter layer, generates photons of in at least two different wavelengths (e.g., WV.I and WV.II), and at least one of the wavelengths (e.g., WV.II) is split into two different beams (e.g., WV.IIa and WV.IIb) (see generally Chan et al. (2004)); several methods and devices to produce such photons in such various wavelengths and beams are known in the art. The PGC is embedded in the glass substrate that comprises the matrix chip of at least one exemplary embodiment of the invention, and a "light guide" can be provided to direct the beams of photons toward at least two precise locations in the microchannel of the microfluidic DNA-stretching microchip (the "linear DNA microchannel").

B. DNA-Stretching Microchip

In a microfluidic DNA-stretching microchip ("DNA stretchchip"), individual DNA molecules (e.g., double-stranded), bound with a sequence-specific dye (or fluorescent tag) and with a nonspecific dye (or fluorescent tag), move through a "post field" and a "funnel," and in the process become linearized or stretched such that one DNA molecule at a time proceeds through a microchannel (the linear DNA microchannel) in which various beams and wavelengths of light are focused on the DNA molecule. In at least one exemplary embodiment of the invention, the width of the linear DNA microchannel is 5 μm. In at least one other exemplary embodiment of the invention, visible light is the form of light.

A DNA stretchchip comprises a series of channels (e.g., a microfluidic inline reaction channel and/or subchannel comprising a post field and a funnel, and a linear DNA microchannel) etched by, e.g., photolithography into a substrate(s) and sandwiched between two substrates (e.g., as detailed below).

As each molecule of DNA passes through the linear DNA microchannel, the stretched molecule encounters at least two sites at which beams of photons are focused. In at least one exemplary embodiment of the invention, there are two sites at which the beams are focused: one site (the first site, as encountered by a molecule of DNA moving in the direction of flow through the linear DNA microchannel) comprises two beams of photons, one beam to detect the site-specific dye (e.g., WV.I) and one beam to detect the nonspecific dye (e.g., WV.IIa). At a second site, at some preset distance further along in the direction of flow in the linear DNA microchannel, an additional beam of photons to detect the nonspecific dye (e.g., WV.IIb) is focused. The two beams detecting the nonspecific dye (e.g., WV.IIa and WV.IIb), which are set apart at some preset distance, are used to establish the length of each molecule of DNA as it passes through the linear DNA microchannel. The beam detecting the site-specific dye is used to identify and analyze each molecule of DNA. A site-specific dye that binds a relatively small site of several basepairs (bps) on a DNA molecule can be utilized for mapping (e.g., identification and/or characterization) the organism from which such genomic DNA was extracted. As a nonlimiting example, the site-specific dye can target, e.g., a 7-8 bp site.

In some instances, the analysis of the positions of the site-specific dyes bound along the length of a double-stranded molecule of genomic DNA is known as "barcoding." Such barcoding of the various molecules of DNA as they pass through the linear DNA microchannel can lead to the identification of a particular type of genomic DNA (e.g., a taxonomic type, e.g., a barcode of a molecule of DNA can identify a particular family, genus, species, strain, etc. when compared with the barcodes in a database).

C. Photon Detector

In at least one exemplary embodiment, the photon detector (e.g., photodetector, light detector, photon counter) component ("PDC") of the invention comprises at least one three-dimensional (3D) photonic crystal that operates at a relatively low temperature and is formed or grown on a glass substrate, and at least one field emission transistor (FET), e.g., a thin-film transistor (TFT), that is also formed on a glass substrate (e.g., a TFT can have a thin film of silicon, and the transistors are fabricated using this thin layer). In at least one further exemplary embodiment, suitable types of transistors other than FETs can be employed. In at least one exemplary embodiment, the PDC is also referred to as a detection layer. In at least one exemplary embodiment, the photon detector is a digital photon detector. In at least one other exemplary embodiment of the invention, glass is the substrate, although any other compatible substrates providing the optical properties necessary for the present invention (e.g., transparent plastics) are also contemplated. For example, several review articles refer to multiple types of substrates useful in a chip of at least one exemplary embodiment of the invention (see, e.g., Mogensen et al., supra; Sia and Whitesides, supra).

In at least one exemplary embodiment of the invention, photons from the several beams (e.g., WV.I; WV.IIa; WV.IIb) focusing on the DNA molecules passing through the linear DNA microchannel are excited by the various dyes (as explained above), and the excited fluorescent light is reflected to a "light guide" toward at least one photon detector. This light guideline inline detector(s) can be implemented with a photonic crystal or crystals (e.g., for the three primary colors). In at least one further exemplary embodiment, a 3D photonic crystal is capable of filtering so that more than one (e.g., two, three) wavelengths of light can reach the photon detector; in another exemplary embodiment, two, three or more different 3D photonic crystals (each filtering to allow a different wavelength) are employed. The photonic crystal(s) of at least one exemplary embodiment of the invention is incorporated into each unit of the matrix chip; the photonic crystal(s) in the chip uses waveguides to direct photons to the novel detector in the chip (inchip detector). The inchip detector is composed of a TFT photodetector. In some exemplary embodiments of the invention, multiple TFTs (e.g., two, three or more TFTs) are incorporated into each unit of the matrix chip (to monitor multiple wavelengths of light). In some further exemplary embodiments, light amplifying TFT(s) are integrated into each unit of the matrix chip for efficient photon emission detection.

However, at least some TFTs, in standard form, are not well suited for direct detection of photons of light. Therefore, in at least one exemplary embodiment of the invention, a (pre-TFT) "gate" is constructed such that a photon of light energy is transduced to energy in the form of electrons that can be directly detected by the TFTs of at least one exemplary embodiment of the invention. The gate comprises a gating material ("porphyrin gate material"), a major component of which is a three-dimensional (3D) single crystal polymer comprising porphyrins. This porphyrin gate material is excitable by photons, e.g., in the visible spectrum, and can function as a semiconductor material. For disclosure related to this polymer and its use as a gate material, see H. Segawa "Nanostructured molecular systems that freely manipulate photons and electrons," available at jstore.jst.go.jp/image/research/pdf/R99/R993100836.pdf; see also Segawa et al. (1994) *J. Am. Chem. Soc.* 116:11193-94; Susumu et al. (1995) *Chem. Lett.* (No. 10):929-30; Segawa et al. (1995) *Synthetic Metals* 71:2151-54; Susumu et al. (1995) *J. Phys. Chem.* 99:29-34; Susumu et al. (1995) *J. Photochem. Photobiol. A: Chem.* 92:39-46; Shimidzu et al. (1995) *J. Photochem. Photobiol. A: Chem.* 92:121-27; Susumu et al. (1996) *Tetrahedron Lett.* 37(46):8399-402; Shimidzu and Segawa (1996) *Thin Solid Films* 273:14-19. Briefly, multiple porphyrins were linked (as porphyrin arrays) in a manner that created molecular systems that carried out photoinduced electron transfer; these porphyrin arrays were directly linked at the meso position. The porphyrin arrays were constructed in one-, two- and three-dimensional molecular architectures (see Segawa, supra).

The matrix analysis area can also comprise a CMOS-type gating mechanism and a CCD-type method of relaying the data from the several units of the matrix. Several methods for implementing such technologies to accomplish the electrical data collection associated with the matrix device of at least one exemplary embodiment of the invention are known in the art.

In at least one exemplary embodiment of the invention, the photon detector of the invention (as described above) reduces or eliminates the need for an AC power supply (as is needed, along with an amplifier, for the photon detectors described in Chan et al. (2004)). This improved photon detector of at least one exemplary embodiment of the invention facilitates considerable reductions in the power requirement (e.g., through the use of TFTs) and the size of the instrument. This is an especially advantageous consideration in light of the fact that each unit (or pixel) of the matrix of at least one exemplary embodiment of the invention comprises a photon detector(s) associated therewith, and, in at least one further exemplary embodiment of the invention (i.e., a 512×512 matrix), 262,144 units are incorporated into the matrix chip. In addition, the units of at least one exemplary embodiment of the invention eliminate the need for external excitation lasers and the related external optics systems disclosed in Chan et al. (2004).

The data produced by the detection of photons in the PDCs of the matrix analysis area (i.e., in at least one exemplary embodiment, the detection of electrons after transduction of the photon signal by the porphyrin-based crystal(s), e.g., porphyrin gate material, interfaced between the linear DNA microchannel and the TFT) is relayed to a predetermined destination, such as a recording device or other storage device, e.g., a computer chip or cache, etc., or a display device or other type of user-perceptible output interface. The coordination of the relay of data from the matrix analysis area to the predetermined destination is accomplished by reading out data (representing detected light) at predetermined timings.

Figure 6A:
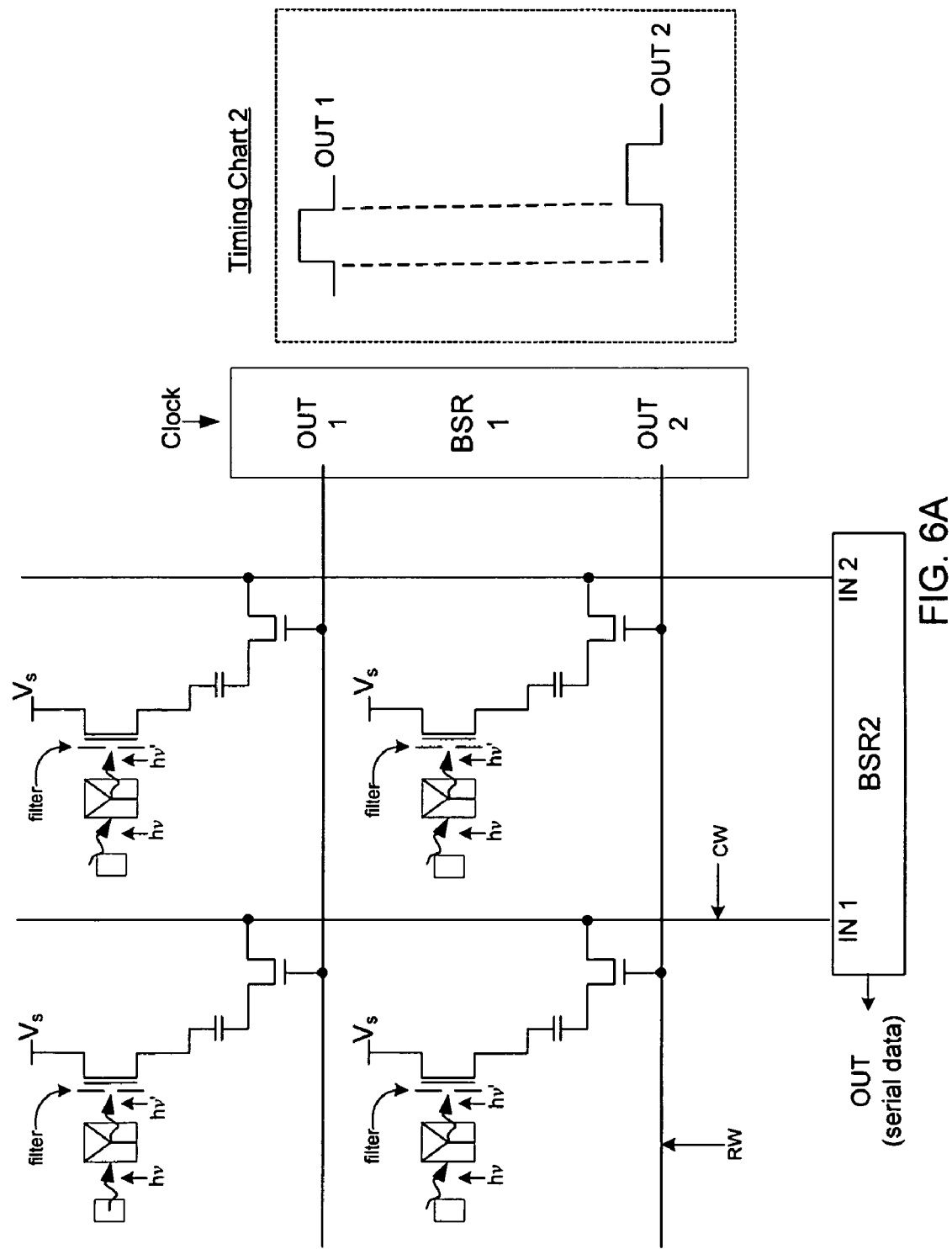
FIGS. 6A-6C depict several aspects of a timing chart of at least one exemplary embodiment of the invention.

At least one exemplary embodiment of the invention is directed to a matrix configuration for reading out data representing detected light (i.e., in some exemplary embodiments, light transduced by the porphyrin gate material), as is depicted in, e.g., FIG. 6A. In at least one further exemplary embodiment of the invention, the matrix is a 512×512 matrix of units (pixels), although for convenience only a two-by-two (2×2) matrix of units is shown in the figure.

The matrix comprises plural row wirings (RW), plural column wirings (CW), capacitors, phototransistors (e.g., the porphyrin gate material/TFTs described above), gating transistors, and binary shift registers (BSR1 and BSR2) that are interconnected in the manner shown in FIG. 6A. In at least one exemplary embodiment of the invention, the transistors are FETs (e.g., TFTs), although in other exemplary embodiments, other suitable types of transistors also can be employed.

Electrical signals representing light (e.g., light transduced by the porphyrin gate material) obtained in the above-described manner are applied to the corresponding phototransistors, and, if the electrical signal has a predetermined threshold voltage level, it is stored as a charge in the corresponding capacitor.

Figure 6B:
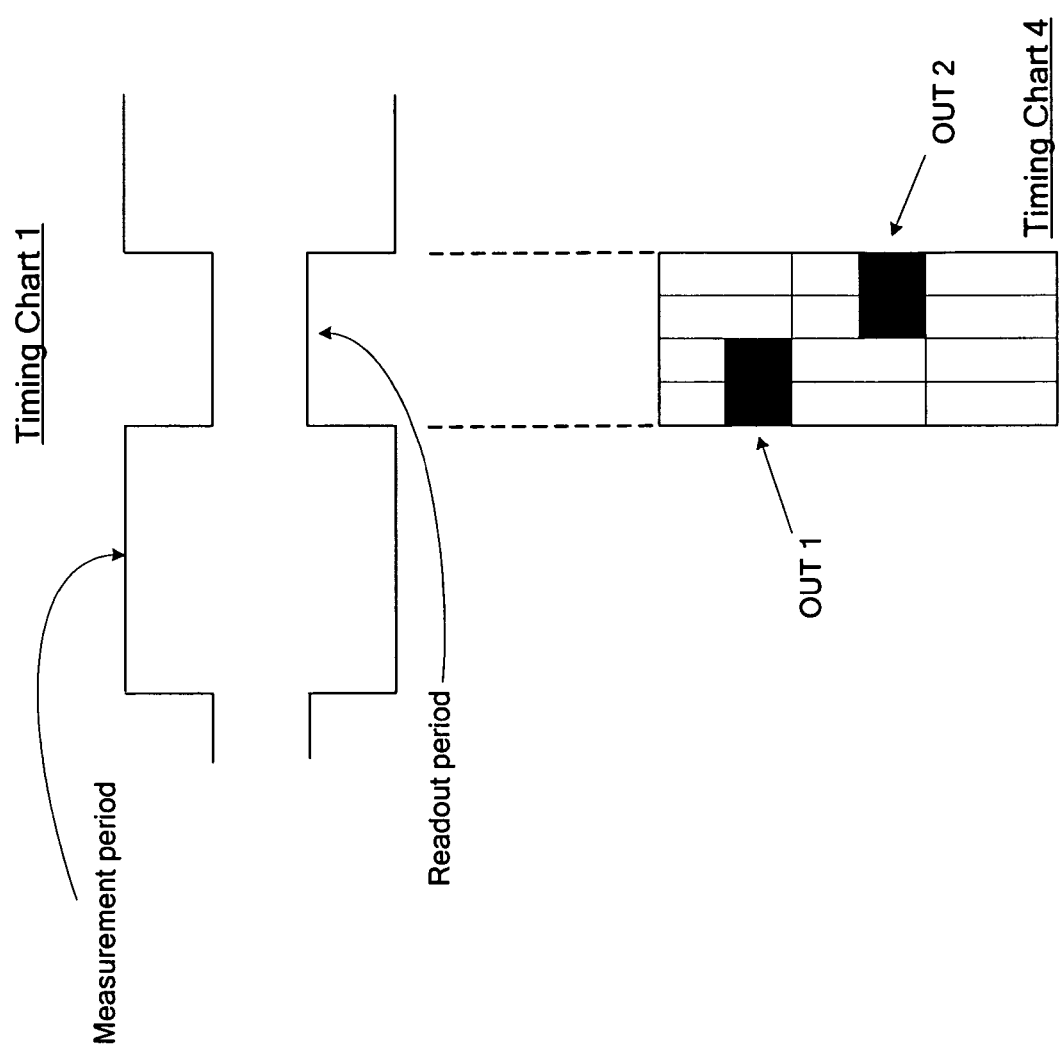
Figure 6C:
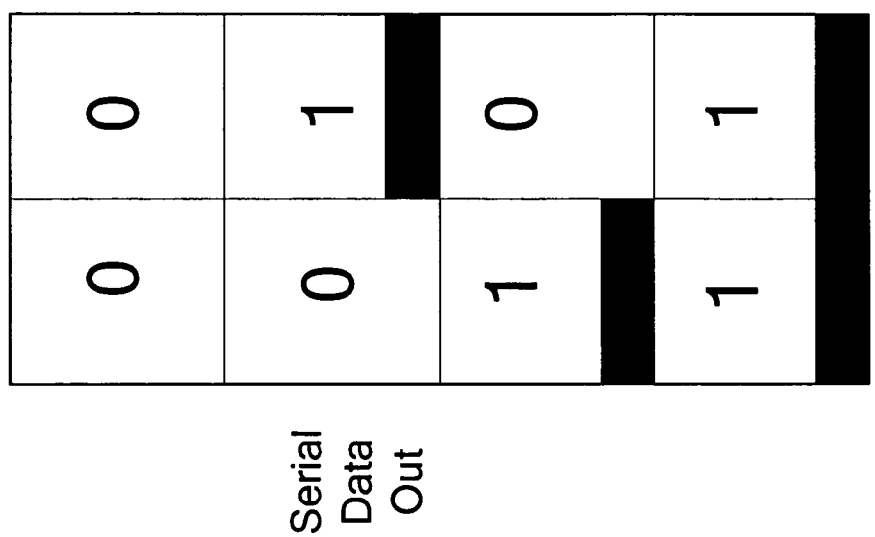

The manner in which signals are read out from the matrix can be understood in view of the timing charts shown in FIGS. 6A-6C. For example, application of a clock pulse (OUT1 or OUT2; FIG. 6A) to the gates of the transistors connected to the corresponding row wiring results in the charge being read from the capacitors. The clock pulses (OUT1, OUT2) are applied to those gates in accordance with Timing Chart 2 (FIG. 6A), in response to a clock pulse generated by an overall system controller (e.g., CPU) (not shown) being applied to the binary shift register (BSR1). The read out charge is then forwarded through the corresponding transistor as a corresponding signal to the corresponding column wiring connected to that transistor. The signal is then forwarded by the column wiring to the corresponding input (IN1 or IN2) of the associated binary shift register (BSR2).

Timing Chart 1 (FIG. 6B) is an example representing how the measurement period (i.e., the period in which the photon is detected) relates to the period in which signals are read out from the capacitors, and the timing at which signals read to the row wirings corresponding to pulses OUT1 and OUT2 are read within each read-out period. As shown in Timing Chart 4 (FIG. 6B), signals are outputted from the capacitors coupled to the row wiring corresponding to clock pulse OUT1 within a first half of the read-out period, and signals are outputted from the capacitors coupled to the row wiring corresponding to clock pulse OUT2 within a second half of the read-out period.

An example of the possible states corresponding to the signals applied to terminals IN1 and IN2 of BSR2 (see FIG. 6A) is shown in Timing Chart 3 (FIG. 6C). Data representing those states is outputted from the BSR2 in series, according to the order in which it is received from the column wirings.

The above-described timing charts, related to the matrix analysis area, comprise at least one exemplary embodiment that can be used in conjunction with the present invention. In other exemplary embodiments, other suitable timings can be employed, as long as the signals can be read out at distinct times for subsequent display, storage and/or processing.

A timing chart or charts can also be employed to control the movement of the sample droplets and subdroplets through the matrix analysis area, and to coordinate (1) the movement of subdroplets through the linear DNA microchannels and (2) the activation of the associated PGCs and PDCs of the units (or pixels) of the matrix analysis area.

The sample droplets or subdroplets pass through the DNA stretchchip at a predetermined rate, as taught generally by Chan et al. (2004). Essentially, the rate is to be set at a near-maximum rate that is still accurate for analysis of the dye-bound DNA molecules. One consideration is that the flow should not be at such a rapid rate that would allow more than one DNA molecule to be present at the same time in the portion of the linear DNA microchannel in which the various beams of light are focused. Another consideration is controlling the rate to avoiding clogging of the post field and the funnel elements of the DNA stretchchip. In at least one exemplary embodiment, a one-femtoliter droplet (i.e., subdroplet, plug, etc.) traverses a DNA stretchchip of at least one exemplary embodiment of the invention in approximately 0.12 msec; in such an exemplary embodiment, the size of the matrix can be approximately 512×512 units (or pixels). This exemplary embodiment is calculated (1) to take into account appropriate levels of resolution, dynamic range, signal-to-noise ratio, etc. for the number of droplets (i.e., subdroplets, plugs, etc.) produced from, e.g., 2.5 µl of eluate comprising genomic material (in turn, produced in the cartridge of at least one exemplary embodiment of the invention from, e.g., 100 µl of blood) and (2) for an approximate analysis time of one hour.

In at least one exemplary embodiment of the invention, the molecular diagnostic device (comprising the cartridge, liquid ejection mechanism, amplification and detection areas, and matrix analysis area of at least one exemplary embodiment of the invention) is portable (e.g., easily movable, convenient for carrying). In at least one further exemplary embodiment, the molecular diagnostic device is hand-held. In some exemplary embodiments, the device is useful to facilitate near-patient (i.e., on-site; away from a hospital or doctor's office) detection and analysis of genomic DNA from, e.g., bacteria. In some further exemplary embodiments, the device employs an AC power source and/or a DC power source (see, e.g., the source voltage (Vs) in FIG. 6A). In at least one other exemplary embodiment of the invention, the device functions without a need for an AC power source; e.g., the device functions exclusively with DC power from an attached (or included), portable (e.g., hand-held) source.

In at least one exemplary embodiment of the invention, the device is expected to produce mostly "zero detection," i.e., most of the data produced by, e.g., the detection area of the device will show zero detection of, e.g., bacterial genomic DNA. In this case, the detection of, e.g., bacterial genomic DNA (i.e., "nonzero detection") will lead to activation of the matrix analysis area of the device and to droplet (i.e., subdroplet, plug, etc.) movement toward and into the matrix chip. In at least one further exemplary embodiment of the invention, such activation and movement in response to nonzero detection is automatic (i.e., is controlled by, e.g., a CPU).

As mentioned above, the barcode of a particular molecule of genomic DNA can serve to identify the taxonomic category of the DNA (e.g., family, genus, species, strain, etc.). The barcode serves as a partial representation of the nucleic acid sequence of the DNA, and can be compared to barcodes representing known taxonomic entities (e.g., in a database of know barcodes). The interpretation of the barcode data can be automated and, in at least one exemplary embodiment, is included in the molecular diagnostic device of the invention. In some exemplary embodiments, the interpretation function is directly connected to the matrix analysis area of the device.

In at least one exemplary embodiment of the invention, the interpretation function of the device is devised to account for the expected variation in sequence that naturally occurs within a given level of taxonomic identification (e.g., at the level of species). In at least one exemplary embodiment, this expected variation can be up to a 75% variation in sequence identity. In at least one further exemplary embodiment of the invention, a probabilistic interpretation feature is incorporated into the interpretation function of the invention to aid in the best-fit identification of the source of the genomic DNA being analyzed by the matrix chip of the device.

In at least one exemplary embodiment of the invention, a database (e.g., comprising barcode information for known or expected pathogens) is included as part of the device. The barcodes of the unknown molecules of genomic DNA being analyzed in the matrix analysis area of the device can thus be compared and contrasted (e.g., matched) to the barcodes in the database to potentially establish the identity of the unknown DNA molecules (i.e., the DNA molecules being analyzed). The molecular diagnostic device of at least one exemplary embodiment of the invention, comprising such a database, can then identify the source organism corresponding to a given DNA molecule being analyzed and, through the interpretation function comprising a probabilistic interpretation feature, provide a calculation of similarity to various levels of taxonomic identification (e.g., with an estimate of probable accuracy). For example, to the extent that the site-specific dyes and the barcoding of a particular exemplary embodiment of the invention are able to accurately identify specific portions of the sequence of an unknown molecule of genomic DNA, a set of barcode data for that molecule of DNA can indicate 100% similarity or identity with a set of barcode data in the database. In this instance, the device can identify, e.g. the genus and species of the source. In another instance, e.g., indicating 83% identity, the device can identify the same genus and species, but with an estimate of accuracy indicating the detected variation. In still another instance, e.g., indicating 50% identity, the device may only identify the genus (with an estimate of accuracy for that level of identification) but give no indication as to species.

In at least one exemplary embodiment of the invention, the database is not included as part of the device; rather the molecular diagnostic device is in wireless communication with a central database.

All scientific articles, reviews, patents, and patent applications cited in the present application are hereby incorporated by reference herein in their entireties.

EXAMPLE

The Example which follows is set forth to aid in the understanding of the invention but is not intended to, and should not be construed to, limit its scope in any way. The Example does not include detailed descriptions of conventional methods that would be well known to those of ordinary skill in the art.

Example 1

The Matrix Analysis Area of the Molecular Diagnostic Device

In at least one exemplary embodiment, the photon generator component (PGC) and the photon detector component (PGC) of a unit (of the matrix analysis area of the molecular diagnostic device) are described as a microcapillary waveguide with integrated optical filter, and depicted in FIGS. 7-11. A single wavelength optical filter is incorporated into half of the microcapillary sandwich during manufacture. This results in the ability to place the photodetector very close to the microcapillary detection tube and thus increase the optical efficiency of receiving the fluorescence emission spectra. In terms of advantages regarding the expense related to the device of at least one exemplary embodiment of the invention, fabrication costs can be much lower due to the fact that the microcapillary manufacturing material is shared with the optical filtering material (e.g., they are the same).

In at least one exemplary embodiment of the invention, the matrix analysis area comprises an emitter layer, a filter layer, and a detector layer.

Figure 7:
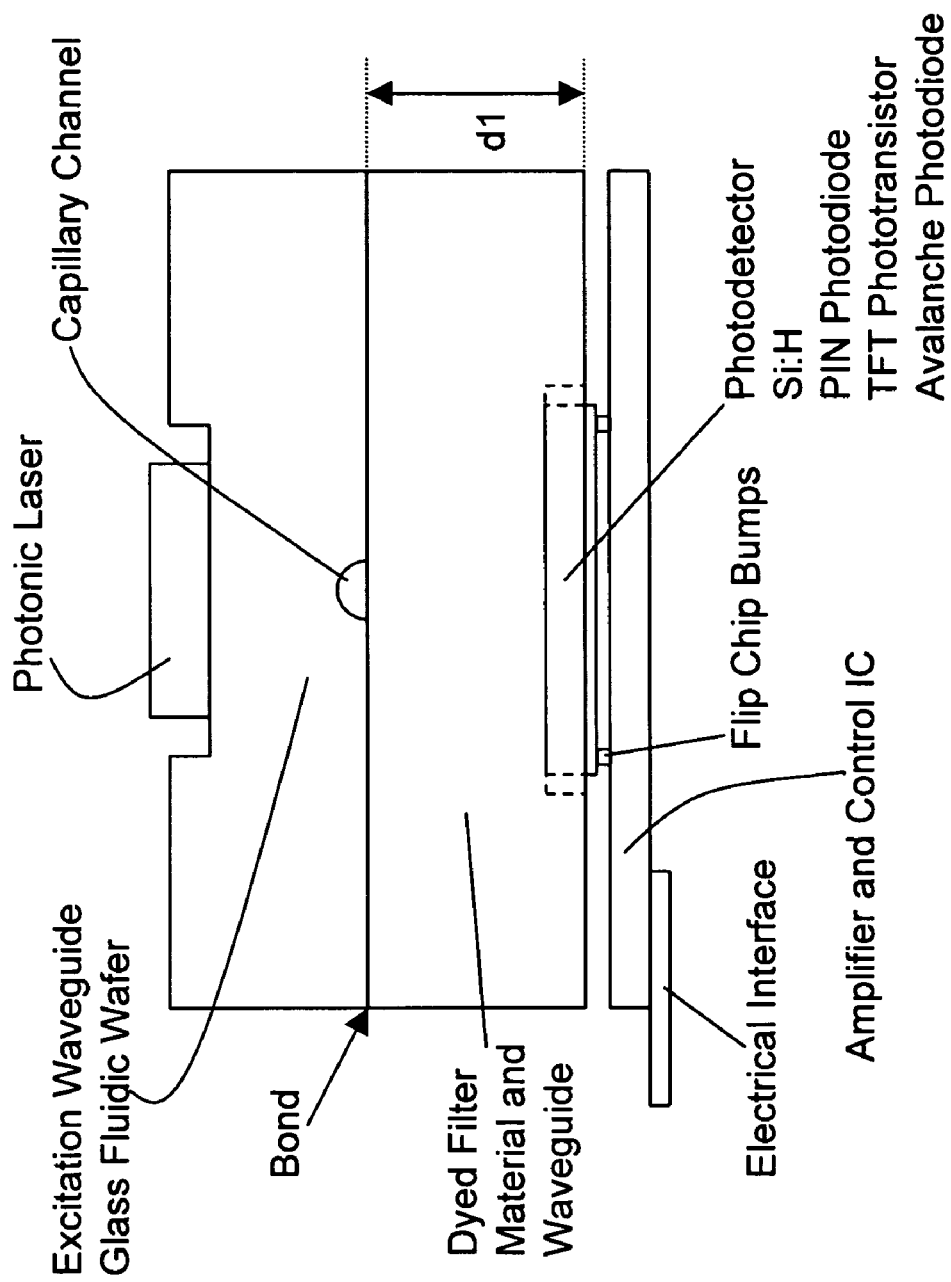
FIG. 7 is a cross-section of a single channel microcapillary (i.e., microfluidic) component of the matrix analysis area of the device in accordance with at least one exemplary embodiment.

FIG. 7 shows a portion of one unit (or "pixel") of the matrix analysis area. As noted above, each unit has at least three components. In this figure, the PGC is the "photonic laser" and the PDC is the "photodetector." The "capillary channel" (e.g., a semicircular capillary channel) serves as a portion of the DNA stretchchip. Two plates of the microcapillary device are shown in FIG. 7. One plate (lower) of the microcapillary device, "dyed filter material and waveguide," is fabricated from the desired colored filter material to control the spectral properties and wavelength(s) of fluorescence emission from the capillary channel to the photodetector; in at least one exemplary embodiment of the invention, the filter layer includes an optical filter doped glass that passes a fluorescent wavelength and blocks the emitter wavelength. In at least one exemplary embodiment, the dimension d1 of the lower plate is in the range of about 10 microns to about 150 microns. In at least one other exemplary embodiment, d1 is about 60 microns. The other plate, an "excitation waveguide glass fluidic wafer" (upper plate in FIG. 7) is optically clear to allow the excitation light (e.g., emitter wavelength) from the laser to reach the reaction area. A microfluidic channel or subchannel (also referred to herein as a capillary channel) within a DNA stretchchip comprises, in at least one nonlimiting exemplary embodiment, an area (containing a post field) of about 50 microns in diameter or width, and a linear DNA microchannel of about 5 microns in diameter or width, with the fluid and DNA moving from the about 50-micron area to the about 5-micron DNA stretchchip microchannel through a funnel-like portion (e.g., reducing the width of the channel from about 50 μm to about 5 μm over a length of approximately 20 μm) (see, e.g., Chan et al. (2004)).

Figure 8:
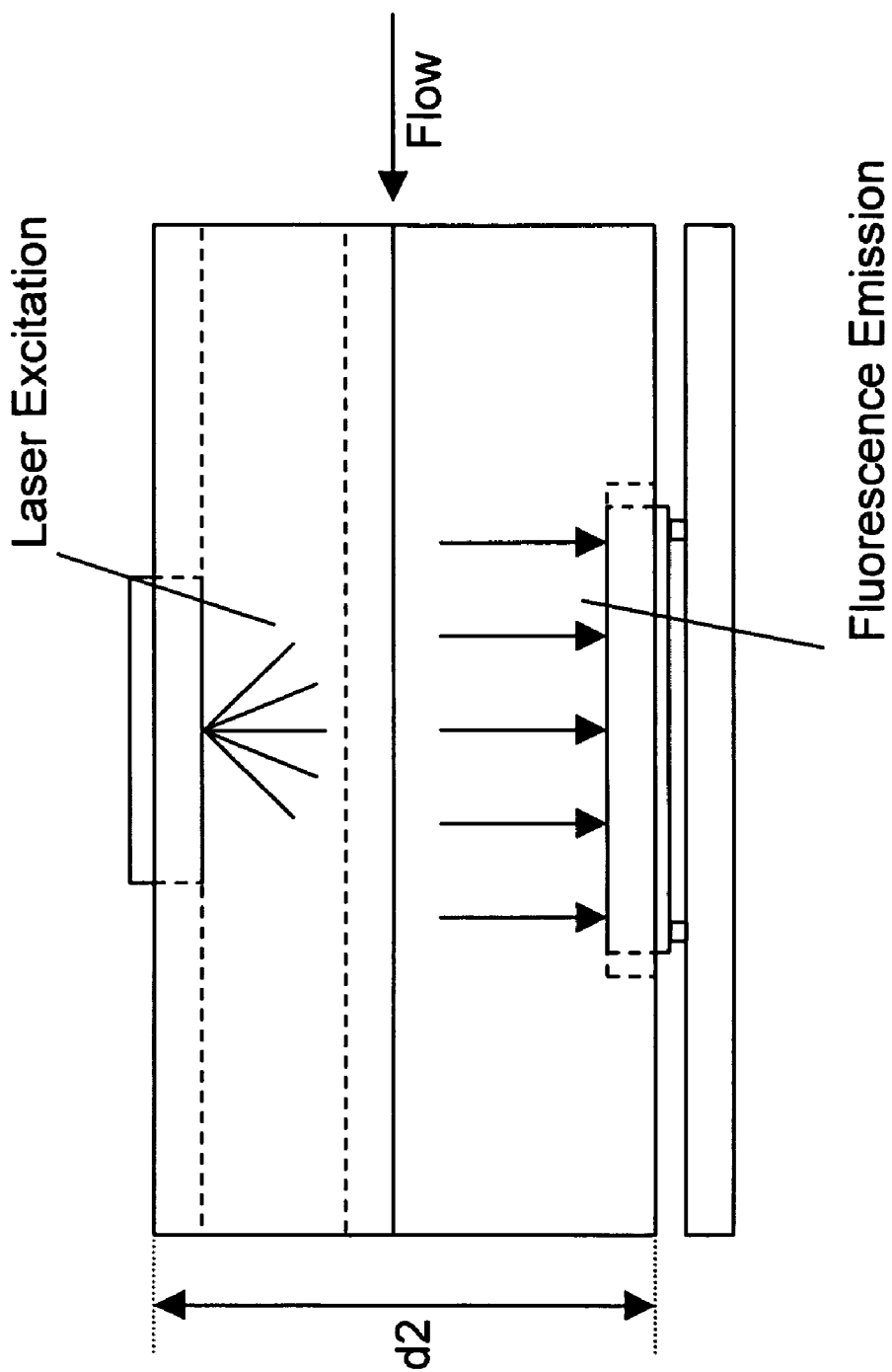
FIG. 8 is an optical diagram generally showing the principle of operation in use as a fluorescence detection system in accordance with at least one exemplary embodiment.

In at least one exemplary embodiment of the invention, the optical filter(s) and waveguide(s) used in the units of the matrix analysis area and involved in the transmission of light ("laser excitation," fluorescence) and "fluorescence emission" as shown in FIG. 8 can comprise one or more optical materials, including but not limited to photonic crystals, organically doped plastic resins, Schott optical glass, colored quartz, colored glass, optical filter doped glass, etc. In at least one exemplary embodiment, the dimension d2 in FIG. 8 is in the range of about 20 microns to about 300 microns. In at least one other exemplary embodiment, d2 is about 120 microns. As stated above, in at least one exemplary embodiment, the filter layer includes an optical filter doped glass that passes a fluorescent wavelength and blocks the emitter wavelength. In at least one further exemplary embodiment, the unit comprises a 3D photonic crystal or crystals.

In at least one exemplary embodiment of the invention, units of the matrix analysis area, and specifically the microfluidic channels contained therein, are manufactured by photolithography. Photolithography can be used to create the microfluidic channel(s), subchannel(s), and/or microchannel(s) in one side of a glass or quartz substrate (the photolithography process can be placed on either side of the substrate). The etched substrate is then bonded to another (e.g., flat) substrate to form an array of microfluidic channel(s). A skilled artisan will recognize that channels of, e.g., semicircular shape in cross-section are produced by bonding an etched substrate to a flat substrate, and that matching etching on both substrates prior to bonding can be employed to produce a channel with a symmetrical shape in cross-section (e.g., circular).

Figure 9:
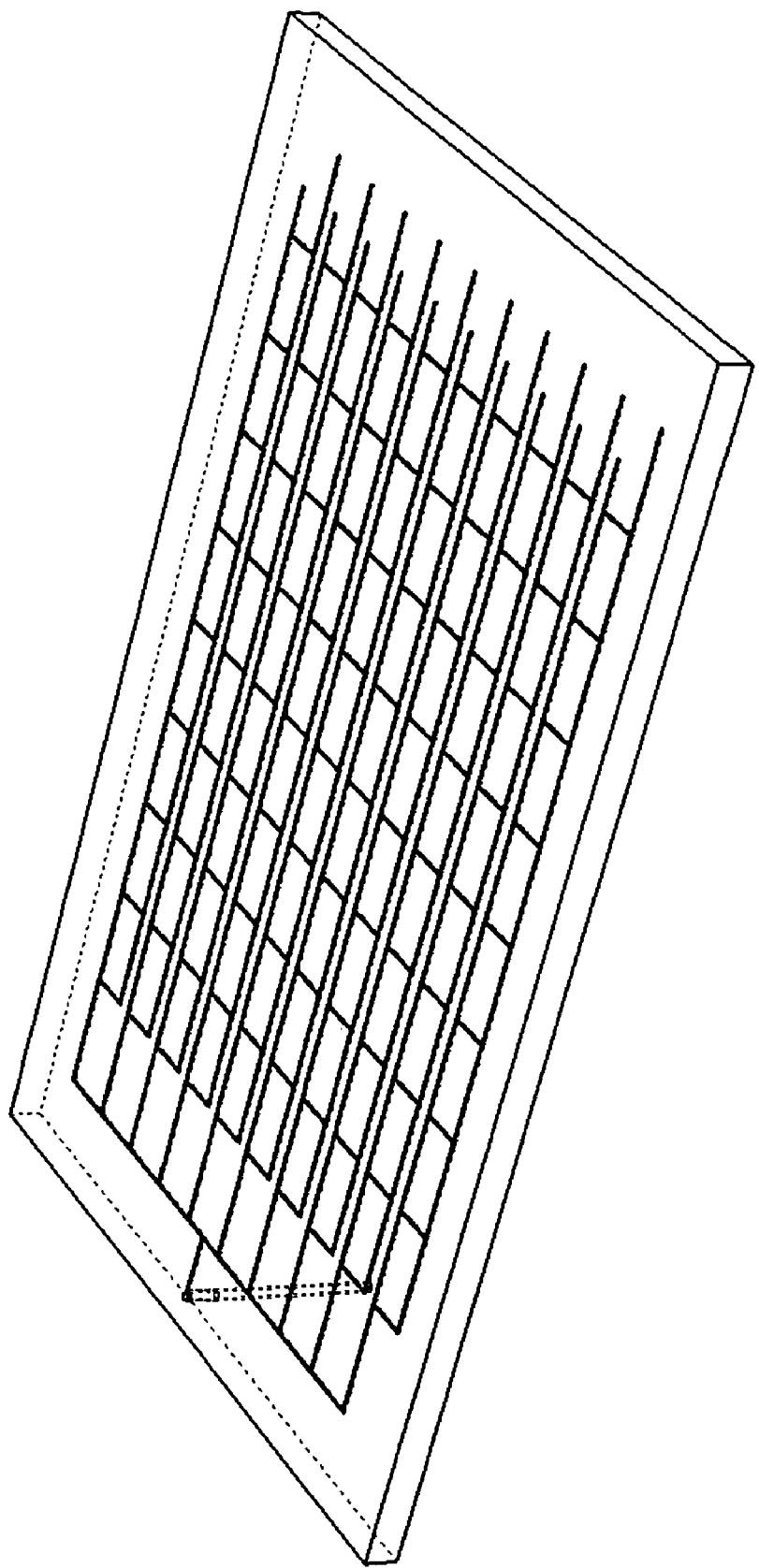
FIG. 9 illustrates the implementation of the matrix (or array) within the matrix analysis area in accordance with at least one exemplary embodiment.
Figure 10:
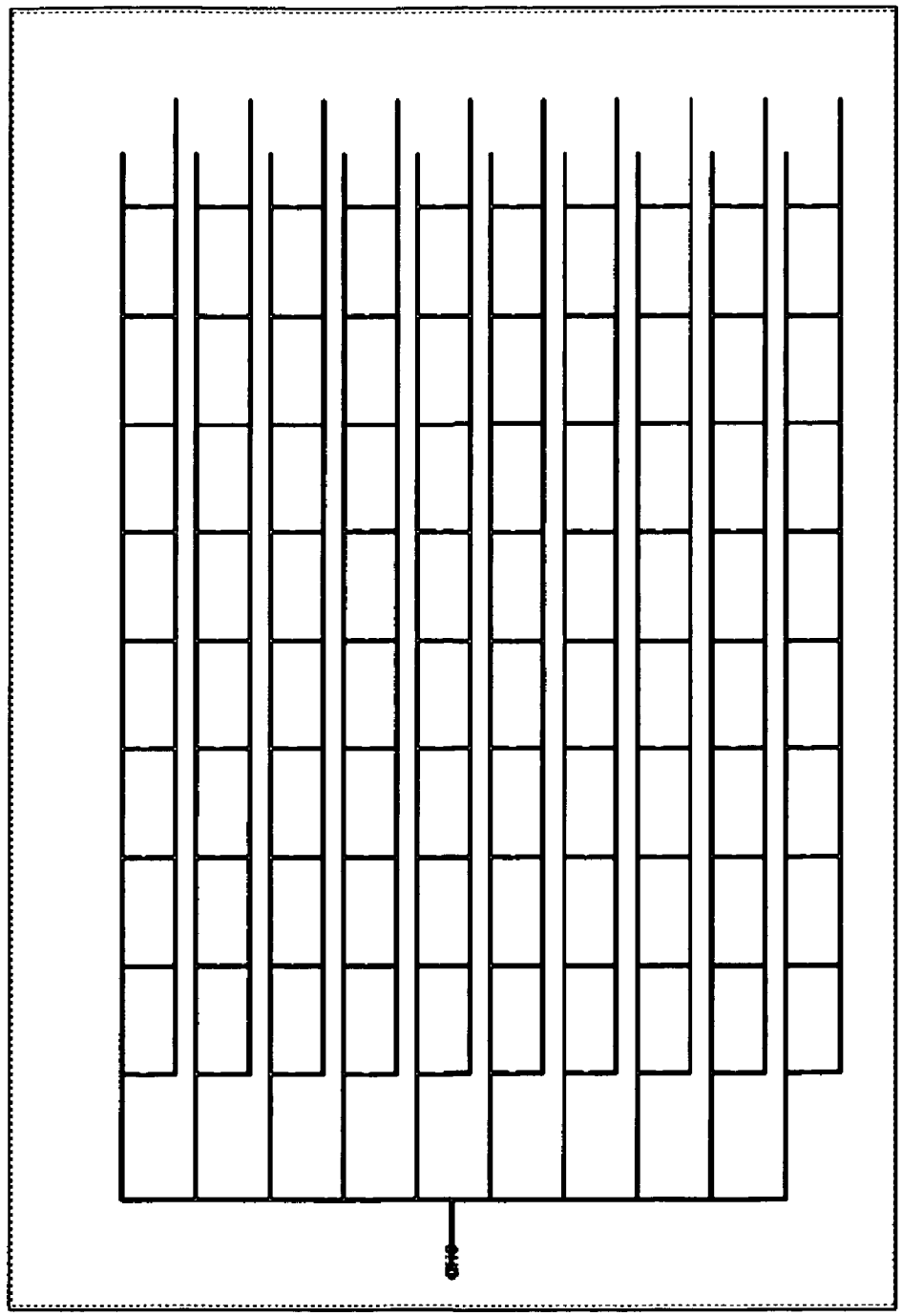
FIG. 10 is a top view of a 90-channel microfluidic array with matrixed optical detection zones in accordance with at least one exemplary embodiment.

In at least one exemplary embodiment of the invention, multiple units, each comprising the three main components of a unit (i.e., PGC(s), DNA stretchchip(s), and PDC(s)), are matrixed together. A plurality of PDCs can be fabricated using a common integrated optical filter, as shown in FIG. 9 (see also a top view in FIG. 10). An advantage of this exemplary embodiment is that one manufacturing piece can form the optical fluorescence filter for many detection channels (i.e., linear DNA microchannels). In practice, when employing such a scheme, one must consider the possibility of optical "crosstalk" and employ methods to avoid this problem.

Figure 11:
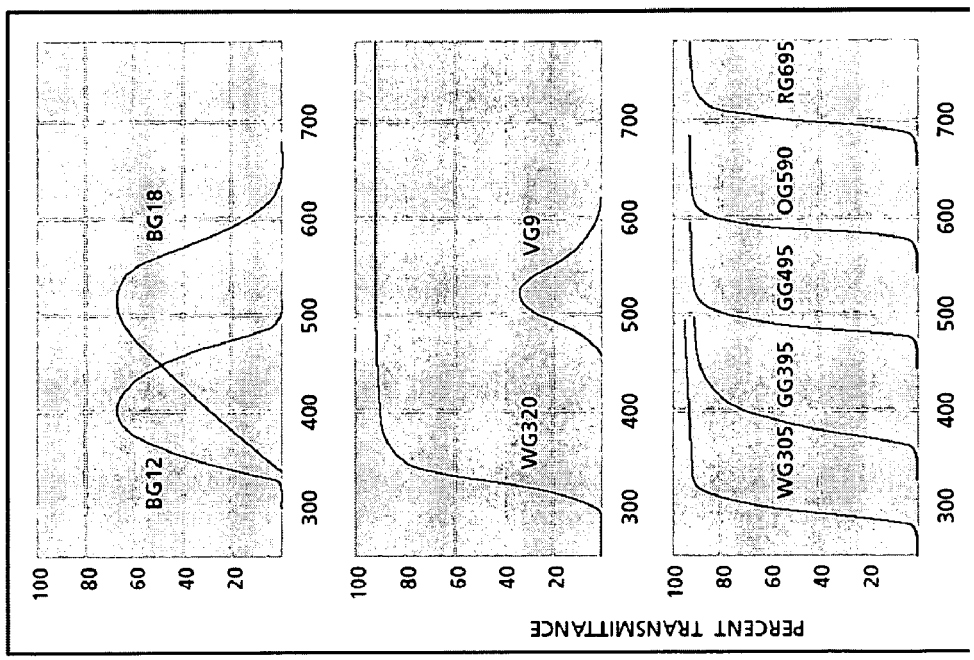
FIG. 11 shows glass filter wavelength characteristics.

A skilled artisan will recognize the importance of the wavelength characteristics and thickness of the glass filter(s) used in the matrix analysis area of the chip. Examples of glass filter wavelength characteristics are shown in FIG. 11. Using known methods in the art of microlithography fabrication, optical glass filter materials can be in the thickness range of 0.1 mm to 480 mm. In at least one exemplary embodiment in the matrix analysis area, the thickness of the materials can be in the range of 0.5 mm to 5 mm, or 1 mm to 3 mm. Using methods and calculations well known in the art, a wavelength (s) and thickness(es) of filter material (e.g., in the filter layer) is selected to separate the excitation spectra from the fluorescence emission spectra with adequate optical SNR (signal-to-noise ratio); thus, the filter layer can comprise a filter, e.g., an optical filter doped glass, that allows a fluorescent wavelength to pass and blocks the wavelength of light from the emitter layer.

In at least one exemplary embodiment of the invention, multiple wavelengths of light (e.g., two, three, or more wavelengths) are monitored by each unit (or pixel) of the matrix chip. In at least one further exemplary embodiment of the invention, multiple TFTs (e.g., two, three or more TFTs) are incorporated into each unit of the matrix chip (to monitor multiple wavelengths of light).

What is claimed is:

1. A cartridge, configured to deliver a sample comprising genomic material, comprising:
    a genomic separation and direction system; and
    an ejector head, wherein a chamber in the ejector head is configured to receive at least a portion of a sample comprising genomic material from the genomic separation and direction system, and wherein the ejector head expels at least a portion of the received sample out of the cartridge as ejected sample droplets, and wherein the ejector head uses thermal energy provided by a thermal energy generator.

2. A cartridge, configured to deliver a sample comprising genomic material, comprising:
    a genomic separation and direction system; and
    an ejector head, wherein a chamber in the ejector head is configured to receive at least a portion of a sample comprising genomic material from the genomic separation and direction system, and wherein the ejector head expels at least a portion of the received sample out of the cartridge as ejected sample droplets, and wherein the ejector head is a piezo jet system.

3. A cartridge configured to isolate genomic material comprising:
    a reaction chamber;
    at least one binding and release substrate, wherein the at least one binding and release substrate lies within the reaction chamber and is configured to bind and release at least a portion of a sample comprising genomic material in response to an electric voltage;
    a genomic separation and direction system; and
    an ejector head, wherein a chamber in the ejector head is configured to receive at least a portion of the sample from the genomic separation and direction system, and wherein the ejector head expels at least a portion of the received sample out of the cartridge as ejected sample droplets; and
    wherein the ejector head uses thermal energy provided by a thermal energy generator.

4. The cartridge according to claim 3, wherein the substrate comprises charge switch material.

5. The cartridge according to claim 3, wherein the substrate is a particle or bead.

6. The cartridge according to claim 3, wherein the substrate is magnetic or paramagnetic.

7. The cartridge according to claim 3, wherein the substrate is bound to the inner surface of the reaction chamber.

8. The cartridge according to claim 3, wherein the volume of at least a portion of the sample released from the substrate is reduced from the volume of the sample.

9. A cartridge configured to isolate genomic material comprising:
a reaction chamber;
at least one binding and release substrate, wherein the at least one binding and release substrate lies within the reaction chamber and is configured to bind and release at least a portion of a sample comprising genomic material in response to an electric voltage;
a genomic separation and direction system; and
an ejector head, wherein a chamber in the ejector head is configured to receive at least a portion of the sample from the genomic separation and direction system, wherein the ejector head expels at least a portion of the received sample out of the cartridge as ejected sample droplets, and
wherein the ejector head is a piezo jet system.

10. A molecular diagnostic device comprising:
at least one cartridge configured to isolate genomic material comprising:
a reaction chamber;
at least one binding and release substrate, wherein the at least one binding and release substrate lies within the reaction chamber and is configured to bind and release at least a portion of a sample comprising genomic material; and
at least one microfluidic chip, wherein the chip is configured to receive at least a portion of ejected sample droplets, wherein the ejected sample droplets are sample droplets ejected from the cartridge, and wherein the chip comprises at least one microfluidic inline reaction channel for receiving the ejected sample droplets.

11. A molecular diagnostic device comprising:
at least one cartridge configured to deliver a sample comprising genomic material, comprising:
a genomic separation and direction system; and
an ejector head, wherein a chamber in the ejector head is configured to receive at least a portion of a sample comprising genomic material from the genomic separation and direction system, and wherein the ejector head expels at least a portion of the received sample out of the cartridge as ejected sample droplets; and
at least one microfluidic chip, wherein the chip is configured to receive at least a portion of ejected sample droplets, wherein the ejected sample droplets are sample droplets ejected from the cartridge, and wherein the chip comprises at least one microfluidic inline reaction channel for receiving the ejected sample droplets.

12. The molecular diagnostic device according to claim 11, wherein the ejector head of the cartridge can be repetitively pulsed to form multiple droplets in sequence at a repetitive pulse rate to achieve a controlled total droplet volume in the microfluidic inline reaction channel of the microfluidic chip.

13. The molecular diagnostic device according to claim 12, wherein the repetitive pulse rate is in the range of about 1 kHz to about 100 kHz.

14. The molecular diagnostic device according to claim 10, wherein the ejected sample droplet has a volume in the range of about 1 picoliter to about 25 picoliters.

15. The molecular diagnostic device according to claim 14, wherein the ejected sample droplet has a volume of about 3 picoliters.

16. The molecular diagnostic device according to claim 12, wherein the total droplet volume is in the range about 3 picoliters to about 100 nanoliters.

17. The molecular diagnostic device according to claim 10, wherein the microfluidic chip further comprises an amplification area within a first temperature-controlled area for the amplification of DNA products, and a detection area within a second temperature-controlled area, and wherein detection of amplified DNA products can occur at more than one temperature.

18. The molecular diagnostic device according to claim 10, wherein the device further comprises a matrix analysis area.

19. A microfluidic chip comprising:
a sample droplet receiving system configured to receive at least a portion of sample droplets comprising genomic material ejected by a cartridge; and
a matrix analysis area, wherein the matrix analysis area comprises:
an emitter layer, wherein the emitter layer emits an emitter wavelength;
a filter layer; and
a detector layer.

20. The microfluidic chip according to claim 19, wherein the filter layer comprises an optical filter doped glass that passes a fluorescent wavelength and blocks the emitter wavelength.

21. The microfluidic chip according to claim 19, further comprising:
at least two channels, wherein the two channels are configured to flow samples comprising genomic material through an amplification area within a first temperature-controlled area for the amplification of DNA products, and a detection area within a second temperature-controlled area for the initiation of fluorescence of DNA products, and wherein detection of amplified DNA products can occur at more than one temperature.

22. A molecular diagnostic device comprising:
at least one cartridge configured to isolate genomic material comprising:
a reaction chamber;
at least one binding and release substrate, wherein the at least one binding and release substrate lies within the reaction chamber and is configured to bind and release at least a portion of a sample comprising genomic material; and
the microfluidic chip according to claim 19, wherein the cartridge ejects sample droplets comprising genomic material into the sample droplet receiving system of the microfluidic chip.

23. The molecular diagnostic device according to claim 22, wherein the matrix analysis area further comprises more than one unit, and wherein each unit comprises at least one photon generator component, a DNA stretchchip, and at least one photon detector component.

24. The molecular diagnostic device according to claim 23, wherein the at least one photon detector component comprises porphyrin gate material.

25. The molecular diagnostic device according to claim 23, wherein the at least one photon detector component comprises three thin-film transistors.

26. The molecular diagnostic device according to claim 22, wherein the device is portable.

27. The molecular diagnostic device according to claim 26, wherein the device is hand-held.

28. A method of characterizing genomic material in a sample, comprising the steps of:
(a) isolating any genomic material in the sample with a cartridge;
(b) ejecting at least one sample droplet from a liquid ejection mechanism in the cartridge into a sample droplet receiving system of a microfluidic chip;
(c) detecting genomic material in the sample droplet; and
(d) analyzing the sample droplet to characterize the genomic material present.

29. The method of claim 28, wherein analyzing the sample droplet comprises comparing a detected barcode from the genomic material in the sample with a database of known barcodes.

30. A molecular diagnostic device comprising:
at least one cartridge configured to deliver a sample comprising genomic material, comprising:
a genomic separation and direction system;
an ejector head, wherein a chamber in the ejector head is configured to receive at least a portion of a sample comprising genomic material from the genomic separation and direction system, and wherein the ejector head expels at least a portion of the received sample out of the cartridge as ejected sample droplets; and
the microfluidic chip according to claim 19, wherein the cartridge ejects the sample droplets comprising genomic material into the sample droplet receiving system of the microfluidic chip.

31. A molecular diagnostic device comprising:
at least one cartridge configured to isolate genomic material comprising:
a reaction chamber;
at least one binding and release substrate, wherein the at least one binding and release substrate lies within the reaction chamber and is configured to bind and release at least a portion of a sample comprising genomic material in response to an electric voltage;
a genomic separation and direction system;
an ejector head, wherein a chamber in the ejector head is configured to receive at least a portion of the sample from the genomic separation and direction system, and wherein the ejector head expels at least a portion of the received sample out of the cartridge as ejected sample droplets; and
the microfluidic chip according to claim 19, wherein the cartridge ejects sample droplets comprising genomic material into the sample droplet receiving system of the microfluidic chip.

32. The molecular diagnostic device according to claim 13, wherein the repetitive pulse rate is about 50 kHz.

33. A molecular diagnostic device comprising:
at least one cartridge configured to isolate genomic material comprising:
a reaction chamber;
at least one binding and release substrate, wherein the at least one binding and release substrate lies within the reaction chamber and is configured to bind and release at least a portion of a sample comprising genomic material in response to an electric voltage;
a genomic separation and direction system;
an ejector head, wherein a chamber in the ejector head is configured to receive at least a portion of the sample from the genomic separation and direction system, and wherein the ejector head expels at least a portion of the received sample out of the cartridge as ejected sample droplets; and
at least one microfluidic chip, wherein the chip is configured to receive at least a portion of ejected sample droplets, wherein the ejected sample droplets are sample droplets ejected from the cartridge, and wherein the chip comprises at least one microfluidic inline reaction channel for receiving the ejected sample droplets.

* * * * *